(12) United States Patent
Eleouët et al.

(10) Patent No.: US 8,252,289 B2
(45) Date of Patent: Aug. 28, 2012

(54) N PROTEIN OF A VIRUS OF THE PARAMYXOVIRIDAE FAMILY-PROTEIN OF INTEREST FUSION PROTEINS

(75) Inventors: Jean-François Eleouët, Breuillet (FR); Sabine Riffault, Jouy En Josas (FR)

(73) Assignee: Institut National de la Recherche Agronomique (INRA), Paris (FR)

( * ) Notice: Subject to any disclaimer, the term of this patent is extended or adjusted under 35 U.S.C. 154(b) by 492 days.

(21) Appl. No.: 12/297,829

(22) PCT Filed: Apr. 18, 2007

(86) PCT No.: PCT/FR2007/000651
§ 371 (c)(1),
(2), (4) Date: Feb. 26, 2009

(87) PCT Pub. No.: WO2007/119011
PCT Pub. Date: Oct. 25, 2007

(65) Prior Publication Data
US 2009/0186337 A1    Jul. 23, 2009

(30) Foreign Application Priority Data

Apr. 18, 2006   (FR) ..................................... 06 03410

(51) Int. Cl.
*A61K 39/00*    (2006.01)
*A61K 39/155*    (2006.01)
(52) U.S. Cl. ................. 424/192.1; 424/211.1; 435/69.3; 435/69.7
(58) Field of Classification Search .................. None
See application file for complete search history.

(56) References Cited

U.S. PATENT DOCUMENTS 6,113,911 A     9/2000 Binz et al.
2004/0224309 A1    11/2004 Cheng et al.

FOREIGN PATENT DOCUMENTS

WO    WO 2006/117456    11/2006

OTHER PUBLICATIONS

Tan et al., Journal of Medical Virology, 2004, 73:105-112.*
Warnes et al., Gene, 1995, 160:173-178.*

Castagne N et al; "Biochemical characterization of the respiratory syncytial virus P-P and P-N protein complexes and localization of the P protein oligomerization domain"; Journal of General Virology, Society for General Microbiology, Spencers Wood, GB, vol. 85, no. Part 6, Jun. 2004, pp. 1643-1653.
Khattar S K et al; "Mutational Analysis of the Bovine Respiratory Synctial Virus Nucleocapsid Protein Using a Minigenome System: Mutations that Affect Encapsidation, RNA Synthesis, and Interaction with the Phosphoprotein"; Virology, Academic Press, Orlando, US, vol. 270, No. 1, 25, Apr. 2000, pp. 215-228.
Murphy LB et al; "Investigations into the amino-terminal domain of the respiratory syncytical virus nucleocapsid preotein reveal elements important for nucleocapsid formation and interaction with the phosphoprotein"; Virology, vol. 307, No. 1, 1, Mar. 2003.
Mavrakis et al; "Rabies virus chaperone: Indentification of the phosphoprotein peptide that keeps nucleoprotein soluble and free from non-specific RNA"; Virology, Academic Press, Orlando, US, vol. 349, No. 2, 21, Feb. 2006, pp. 422-429.
Khattar S K et al; "Mapping the domains on the Phosphoprotein of bovine respiratory syncytical virus required for N-P and P-L interactions using a minigenome system"; Journal of General Virology, Society for General Microbiology, Spencers Wood, GB, vol. 82, No. 4, Apr. 2001.
Choi KS et al; "Rapid competitive enzyme-linked immunosorbent assay for detection of antibodies to peste de petits ruminants virus"; Jo. Ni. Clin. Diagn. Lab Immunol, vol. 12, No. 4, 21, Apr. 2005, pp. 542-547.
Beck A. et al; "Synthesis and characterization of Respiratory Syncytical Virus protein G related peptides containing two disulfide bridges"; J Pept Res, vol. 55, No. 1, 21, Jan. 2000, pp. 24-35.
Chen I et al; "Site-specific labeling of proteins with small molecules in live cells"; Current Opinion in Biotechnology, London, GB, vol. 16, No. 1, Feb. 2005.
Stitetelaar et al; "In vitro processing and presentation of a lapidated cytotoxic T-cell epitope derived from measles virus fusion protein"; Vaccine, vol. 20, No. 1-2, Oct. 12, 2001.

* cited by examiner

*Primary Examiner* — Stacy B. Chen
(74) *Attorney, Agent, or Firm* — B. Aaron Schulman; Stites & Harbison, PLLC

(57) ABSTRACT

The invention relates to N protein-protein of interest fusion proteins, optionally in the form of soluble N protein-protein of interest/P protein complexes, the N and P proteins being proteins of a virus of the Paramyxoviridae family. When the protein of interest is an antigen, the invention relates also to vaccinal compositions and diagnostic reagents comprising those N protein-antigen fusion proteins or those N protein-antigen/P protein complexes. The N protein-protein of interest fusion protein can also be used as a "vector" for transporting into cells therapeutic molecules of interest, such as antivirals or anticancer agents.

4 Claims, 4 Drawing Sheets

Figure 1:
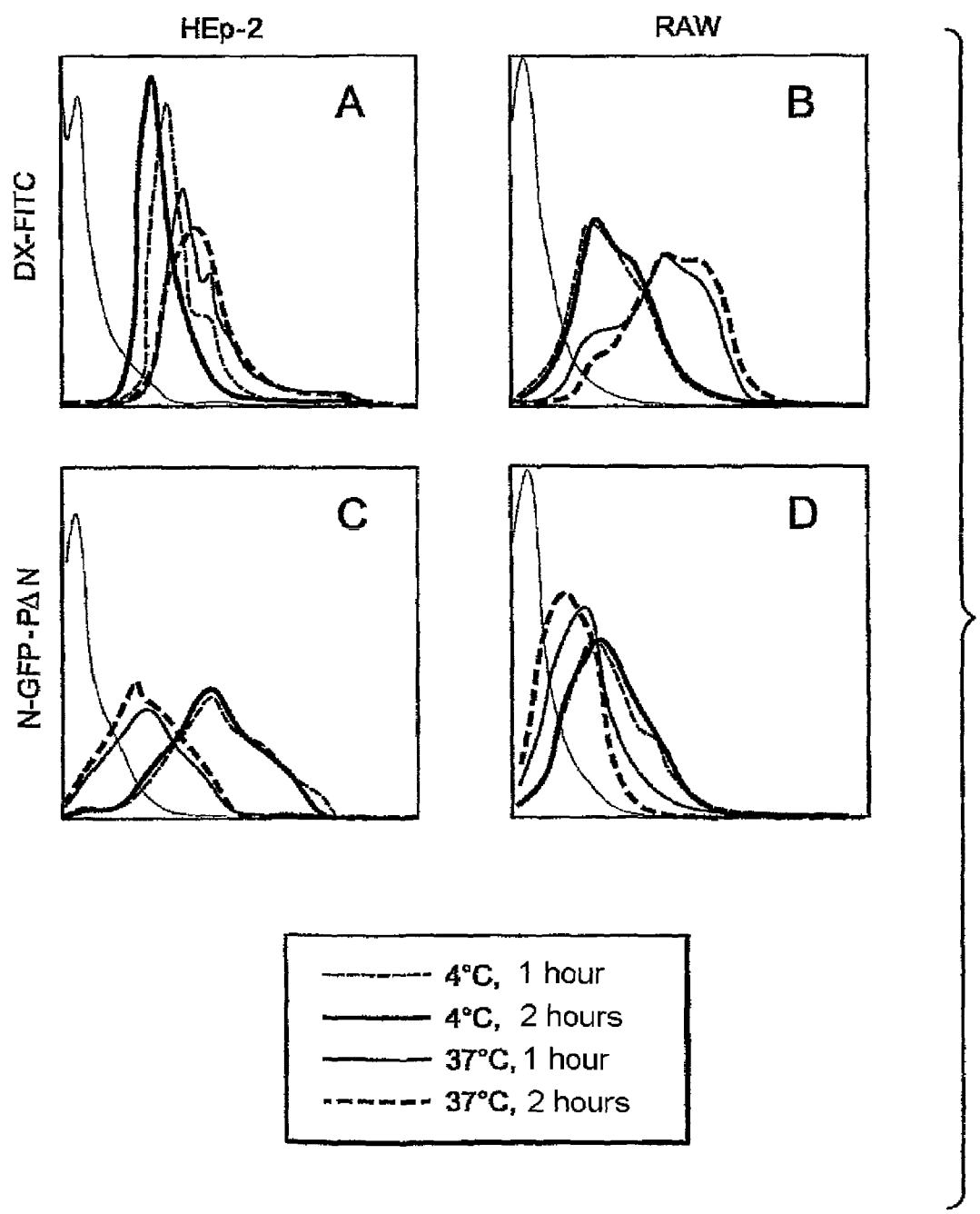

N PROTEIN OF A VIRUS OF THE PARAMYXOVIRIDAE FAMILY-PROTEIN OF INTEREST FUSION PROTEINS

The invention relates to N protein-protein of interest fusion proteins, optionally in the form of soluble N protein-protein of interest/P protein complexes, the N and P proteins being proteins of a virus of the Paramyxoviridae family. When the protein of interest is an antigen, the invention relates also to vaccinal compositions and diagnostic reagents comprising those N protein-antigen fusion proteins or those N protein-antigen/P protein complexes. The N protein-protein of interest fusion protein can also be used as a "vector" for transporting into cells therapeutic molecules of interest, such as antivirals or anticancer agents.

Respiratory syncytial virus (RSV) is responsible for infantile bronchiolitis (500,000 children are affected each year in France). There is no truly effective preventive treatment (vaccine) or antiviral against that disease. The same disease exists in bovine, affecting 70% of calves in the first year, where the mortality can reach 20%, and bovine RSV is the main agent that is responsible for serious respiratory diseases in calves. The clinical presentation is identical with that in humans. This virus belongs to the Mononegavirales order and to the Paramyxoviridae family. The viral particles are surrounded by a lipid envelope containing two major proteins, the fusion protein (F) and the glycoprotein (G). Inside the particles there is a single-stranded RNA of negative polarity of approximately 15 kb, associated with the nucleocapsid protein (N). That RNA-N complex constitutes the matrix of the polymerase complex constituted by the L protein (large fragment), which is the RNA-dependent RNA polymerase, and its cofactor P (phosphoprotein), which are also present in the virions.

It has not hitherto been possible to purify the N protein in soluble form because, when expressed in recombinant form, it binds spontaneously and non-specifically to the cellular RNAs, forming insoluble structures of very high molecular weight (Méric et al. 1994 Virus Res. 31(2):187-201; Bhella et al., 2002 Journal of General Virology; 83, 1831-1839). The inventors have developed a method for obtaining the nucleocapsid (N) protein of respiratory syncytial virus (RSV) in soluble recombinant form having a ring-like structure, and its use as a vaccine. The N protein is in the form of very regular rings having a diameter of approximately 7 nm, containing 10 molecules of N protein and a RNA of bacterial origin of approximately 70 bases. The N protein is coexpressed in *E. Coli* with the phosphoprotein (P) of RSV, more particularly its C-terminal portion, fused to glutathione-S-transferase (GST), which allows the complexes to be purified by affinity with sepharose-glutathione beads. Those ring-like structures induce a strong immune response in the mouse, especially by intranasal administration, also in the absence of adjuvant. That method is the subject of a patent application filed in France on 29 Apr. 2005 under number FR 05 04 426.

The inventors have now shown that it is possible to use those ring-like structures as a vaccinal vector. The feasibility of that technology has been demonstrated by fusing the N protein to another protein, GFP (green fluorescent protein), by plasmid construction. It has been coexpressed in *E. Coli* with the C-terminal portion of the P protein (amino acids 161-241) fused to GST. Analysis of the purified structures using an electron microscope showed that the grafting of GFP at the C-terminal end of the N protein still allows the N protein to be produced in the form of rings having a diameter of approximately 10 nm. The N-GFP fusion proteins are fluorescent.

Because the N—RNA rings are extremely immunogenic, the inventors injected those structures into mice in order to see if they could induce a strong antibody response, especially against GFP. The responses were compared with those obtained against the "normal" GFP protein also purified in recombinant form from *E. coli*. The results obtained showed a markedly stronger response to GFP (approximately 40 times greater for the first experiment) when the ring-like structures are used.

The possibility of fusing a protein of interest to the N protein and of purifying the complexes in the form of soluble rings on an industrial scale and at moderate cost (in particular in *E. Coli*) will thus permit the development of vaccines against any type of epitope that is not very immunogenic or is not immunogenic when injected on its own.

The inventors have further shown that those N protein-GFP/P protein structures are adsorbed and are effectively internalized by different cell types. Those results therefore highlight the value of such N protein-protein of interest fusions, optionally in the form of a N protein-protein of interest/P protein complex, as an antigen vector for vaccination, or more generally as molecules of therapeutic interest.

Definitions

The "Paramyxoviridae" family encompasses the Paramyxovirinae and Pneumovirinae subfamilies. The Paramyxovirinae include the genera Respirovirus, the prototype virus of which is the Sendai virus, Rubulavirus (especially the mumps virus), Morbilivirus, such as the measles virus. Each of the genera Respirovirus and Rubulavirus groups together strains of the parainfluenza virus. The Pneumovirinae subfamily groups together two genera, the Pneumovirus and the Metapneumovirus, the latter including the human Metapneumovirus. Human respiratory syncytial virus (RSV) constitutes the prototype virus of the genus Pneumovirus belonging to the Pneumovirinae subfamily. The Pneumovirus also include the bovine and murine strains of RSV.

Unless specified otherwise, "respiratory syncytial virus" is generally understood as meaning RSV, whatever its form (human, bovine, etc.), the subgroup (for example subgroups A, B and S identified in human RSV) or the strain in question.

"N protein" denotes the nucleocapsid protein of the Paramyxoviridae, which forms helical structures to surround the viral genome. The N protein of human RSV Long strain has a sequence of 391 amino acids which is described by SEQ ID NO:1. The N protein of bovine RSV likewise comprises 391 amino acids (see SEQ ID NO:2). A N protein of the Sendai virus (strain Hamamatsu), of the measles virus (strain Edmonston B), of the mumps virus (strain SBL-1) and of the human Metapneumovirus (strain 00-1) are also described in the Swissprot database under accession numbers Q9DUE3 (SEQ ID NO:3), Q89933 (SEQ ID NO:4), P21277 (SEQ ID NO:5) and Q91F57 (SEQ ID NO:6), respectively.

The expression "protein" denotes the phosphoprotein or P protein forming part of the polymerase complex of a virus of the Paramyxoviridae family. The P protein is a cofactor of the viral polymerase (replicase/transcriptase) and can be phosphorylated. The sequences of the P protein of Paramyxoviridae are known to the person skilled in the art. For example, the P protein of human RSV Long strain has a sequence of 241 amino acids, which has been deposited in the Swissprot database under accession number P12579. That sequence is shown in SEQ ID NO:7. The P protein of bovine RSV also comprises 241 amino acids (SEQ ID NO:8). A P protein of the Sendai virus (strain Harris), of the measles virus (strain Edmonston B), of the mumps virus (strain SBL-1) and of the human Metapneumovirus (strain 00-1) are also described in the Swissprot database under accession numbers $PO_{4859}$ (SEQ ID NO:9), CAA91364 (SEQ ID NO:10), P19717 (SEQ ID NO:11) and Q91KZ5 (SEQ ID NO:12), respectively. The expression "protein" may denote a whole P protein, a truncated P protein or a fragment of the P protein.

The P protein of the Paramyxoviridae forms homooligomers, in particular homotetramers, for example in the Sendai virus or RSV. In the case of RSV, a domain of the P protein capable of oligomerization (P—P oligomerization) has been mapped in the region of amino acids 120 to 150 of that protein (Castagné et al., 2004; Journal of General Virology; 85: 1643-1653). Thus, for example, the fragment constituted by amino acids 161 to 241 of the P protein of RSV does not form oligomers. The oligomerization domain of the P protein of the Sendai virus has been described by Tarbouriech et al. (2000; Nature Structural Biology; 7, 777-781) as being constituted by residues 320 to 446 of the P protein. On the other hand, the P oligomerization region has been identified in the region of amino acids 304-376 for the P protein of the measles virus (Johannson et al., 2003; Journal of Biological Chemistry; 278, p. 44567-44573).

The sequences of the P and N proteins described above are illustrative in nature, it being possible for the sequences to exhibit variations according to the particular strain under consideration for a given virus. Accordingly, the amino acid positions mentioned in the remainder of the application are indicated relative to those reference sequences. The person skilled in the art is wholly capable of identifying the corresponding domains in virus strains other than those exemplified, especially with the aid of sequence alignments carried out, for example, using softwares such as Clustalw.

The coding sequences of these N and P proteins of viruses of the Paramyxoviridae family are also known to the person skilled in the art.

The term "protein label", also called "protein tag", denotes a protein which is used fused to a protein of interest in order to facilitate the purification thereof. Protein tags are known to the person skilled in the art. Examples of protein tags include glutathione-S-transferase (GST) or the histidine tags, which are sequences generally comprising a chain of from 4 to 10 histidine residues.

A "protein of interest" denotes any protein, polypeptide or peptide (these terms being used indiscriminately), such as, for example, a marker protein, or a protein of therapeutic or vaccinal interest.

A protein of interest may be, for example, the protein GFP (green fluorescent protein) coded for by the gfp reporter gene.

A protein of therapeutic interest may be, for example, an antiangiogenic polypeptide, for example RGD or a sequence including RGD, endostatin, or a proapoptotic polypeptide such as the apoptosis-inducing factor (AIF), which can be used as anticancer agents, a polypeptide capable of interacting specifically with viral proteins and interfering with the mechanisms that permit the replication of a virus, or a toxin.

The heterologous protein of interest may be an antigen, in particular an antigenic protein of vaccinal interest. "Antigen" or "Ag" is understood as being a sequence of peptidic or glycopeptidic nature that is capable of inducing an immune response in a host to which it is administered. Accordingly, an antigen may be a protein or part of a protein (polypeptide) or alternatively a small peptide potentially corresponding to an epitope.

An "epitope" is the part of an antigen that is recognized by an antibody or by a lymphocyte receptor. A (linear) epitope is generally constituted by a sequence of from 7 to 15 amino acids. An antigen within the scope of the invention may be constituted by an epitope, may comprise an epitope or may be an antigenic protein.

Preferably, the antigen is an antigen derived from a pathogenic microorganism, such as a virus, a bacterium, a fungus or a parasitic metazoan or protozoan organism.

Examples of viruses include human immunodeficiency virus (HIV), hepatitis B virus (HBV), hepatitis C virus (HCV), herpes virus (*Herpes simplex*), flu virus (influenza or avian flu virus), occidental Nile virus, yellow fever virus, cytomegalovirus, papillomavirus (HPV), Epstein-Barr virus (EBV), RSV, Dengue virus and Chikungunya virus.

Examples of parasites include the parasites responsible for malaria (Plasmodium, in particular *P. falciparum, P. vivax, P. ovale* and *P. malariae*) and for trypanosomiasis (in particular sleeping sickness (*T. brucei*) and Chagas disease (*T. cruzi*)).

The pathogen may also be a fungus such as *Candida albicans*, which is responsible for candidosis.

Bacteria may be, for example, *Heliobacter pylori, Clostridium tetani, Mycobacterium tuberculosis* or *Mycobacterium bovis*.

For example, an antigen may be GFP, a viral glycoprotein such as the RSV fusion protein (F), influenza virus hemagglutinin, or HIV gp120 protein, a bacterial anatoxin such as the tetanus anatoxin, or an epitope thereof.

N Protein-Protein of Interest Fusion Proteins and their Preparation

The invention relates to a N protein-protein of interest fusion protein comprising a N protein of a virus of the Paramyxoviridae family and a protein of interest fused in frame at the C-terminal end of the N protein.

In the context of the present invention, the protein of interest is specifically fused at the C-terminal end of the N protein. This construction allows the N protein to be incorporated into ring-like structures having a diameter of approximately 10 nm when a method for producing the fusion protein as described hereinbelow is used.

Said virus of the Paramyxoviridae family may be a Paramyxovirinae or Pneumovirinae. In particular, the virus may be selected from the group constituted by the mumps virus, the measles virus, the human Metapneumovirus and the parainfluenza virus. Preferably, the virus is a Pneumovirus, in particular human or bovine respiratory syncytial virus (RSV).

The N protein present in the fusion protein according to the invention generally has the amino acid sequence of a native N protein, that is to say a N protein naturally present in a Paramyxoviridae virus.

However, for the purposes of the expression of the fusion protein, sequence modifications may be introduced at the C-terminal end of the N protein, provided that the N protein retains its ability to interact with the P protein. In particular, a native N protein of a Paramyxoviridae virus may have been modified in the region defined by the last 25, preferably the last 20, 15, 10 or 5, C-terminal amino acids.

Such modifications typically consist in the deletion, substitution and/or insertion of one or more amino acids (for example from 1 to 25, or from 1 to 20, from 1 to 15, from 1 to 10, or alternatively from 1 to 5 contiguous or non-contiguous amino acids) in the C-terminal sequence of the N protein.

An example of a sequence modification of the N protein may consist in the deletion of the 6 or 12 C-terminal amino acids, the truncated N proteins (NΔ6C and NΔ12C) still being capable of interacting with the P protein.

The protein of interest may be a marker protein, a protein of therapeutic interest or of vaccinal interest, without being limited thereto. Preferably, the protein of interest is an antigenic protein.

Furthermore, the protein of interest may itself be a fusion protein. For example, it may be a construction comprising GFP fused in frame, at its C-terminal end, with a protein of interest, the GFP itself being fused in frame at the C-terminal end of the N protein (that is to say a N protein-GFP-protein of interest fusion protein).

Preferably, the construction N-GFP-protein of interest may include between the N and GFP proteins a linker sequence having the sequence KLRILQSTVPSERPQASGVYMGN-LTTRGPVAT (SEQ ID NO:32), which permits optimization of the production yield of the N-GFP fusion protein (see Example 6) and therefore of the N-GFP-protein of interest fusion protein.

The protein of interest may be in particular a GFP-antigenic protein or GFP-protein of therapeutic interest fusion protein. It may also be a chimeric protein comprising a "linker sequence" fused to the protein of interest. The linker sequence is a polypeptide which typically comprises up to 30 amino acids, preferably up to 20 amino acids, more preferably up to 10 amino acids, and which acts as a spacer between the N protein and the protein of interest, which enables each of those proteins to be correctly folded.

Accordingly, according to an embodiment, the protein of interest is an antigen and the fusion protein according to the invention is a N protein-antigen ("N—Ag") fusion. Preferably, it is a fusion protein of the N protein of human or bovine RSV with an antigenic protein.

According to another embodiment, the protein of interest is a protein of therapeutic interest and the fusion protein according to the invention is a N protein-protein of therapeutic interest fusion. Preferably, it is a fusion protein of the N protein of human or bovine RSV with a protein of therapeutic interest.

Advantageously, a tag (such as a histidine tag) may be fused at the N-terminal end of the N protein in order to facilitate the purification of the N protein-protein of interest fusion proteins.

Alternatively, purification of the N protein-protein of interest fusion proteins may be carried out by coexpressing said fusion protein with a P protein of the Paramyxoviridae virus, in particular a P protein fused to GST, as will be explained in detail hereinbelow.

Any conventional molecular biological, microbiological or recombinant DNA technique may be used to produce the fusion proteins according to the invention. Such techniques are within the scope of the person skilled in the art and have been described, especially in Sambrook, Fritsch & Maniatis, Molecular Cloning: A Laboratory Manual, Second Edition (1989) Cold Spring Harbor Laboratory Press, Cold Spring Harbor, N.Y. ("Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription and Translation [B. D. Hames & S. J. Higgins, eds. (1984)]; Animal Cell Culture [R. I. Freshney, ed. (1986)]; Immobilized Cells and Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

The invention therefore relates also to the nucleic acids coding for the above-mentioned N protein-protein of interest fusion protein.

A "coding sequence" denotes a nucleotide sequence which, when expressed, results in the production of a RNA, of a polypeptide, of a protein, etc. A coding sequence of a protein generally contains a start codon (ATG) and a stop codon.

"Express" or "expression" means to permit or enable the information contained in a gene or a DNA sequence to manifest itself, for example by producing a protein by activation of the cell functions involved in the transcription and translation of the genetic sequence or of corresponding DNA. The term "coexpression" is used when the information contained in two genes or DNA sequences is expressed in the same host cell.

The invention therefore includes nucleic acids (cDNA, genomic DNA, synthetic DNA, or RNA) encoding the N protein-protein of interest fusion proteins. The nucleic acid may be double-stranded or single-stranded (that is to say a sense or antisense strand). The nucleic acids are not limited to the sequence encoding the fusion protein and may include coding or non-coding sequences upstream or downstream of the sequence encoding the fusion protein.

The sequence coding for the fusion protein according to the invention is a hybrid or chimeric sequence containing at least two parts, consecutively in the 5'-3' direction a part coding for the N protein and a part on the 3' side coding for the protein of interest. When the protein of interest is itself a fusion or when a tag is attached to the N protein, the coding sequence contains the appropriate number of parts. Between each of the parts, codons may code for a linker sequence.

The invention relates also to expression vectors containing the nucleic acids coding for the N protein-protein of interest fusion protein. Such vectors may contain a transcription-regulating element functionally linked with the DNA.

A coding sequence is "functionally linked with" transcription and translation control sequences when a RNA polymerase transcribes the coding sequence into RNA, in particular into mRNA, which may subsequently be spliced, if it contains introns, and translated into the protein encoded by the coding sequence.

The expressions "vector", "cloning vector" and "expression vector" denote the vehicle by which a DNA or RNA sequence (for example a heterologous gene) can be introduced into a host cell in order to transform the host cell and promote the expression of the sequence that has been introduced. Examples of vectors include plasmids, phages, viruses. The most common vectors are plasmids, which are autonomous replication units, generally of bacterial origin, and which can be in the form of double-stranded DNA. The plasmids can readily integrate an exogenous DNA sequence, which can then readily be introduced into a suitable host. A plasmid vector generally contains a coding DNA sequence, a promoter DNA sequence and has one or more restriction sites permitting the introduction of exogenous DNA. Non-limiting examples of plasmids include the plasmids pKK (Clonetech), pUC and pET (Novagen, Inc., Madison, Wis.), pRSET or pREP (Invitrogen, San Diego, Calif.), pMAL (New England Biolabs, Beverly, Mass.), or pGEX-4T-3 (Pharmacia).

The invention relates also to host cells containing the expression vectors according to the invention. These host cells are "transformed" with said vectors.

"Host cell" is understood as meaning any cell or organism which is selected, modified, cultivated or engineered for the production of a substance by the cell, for example the expression by the cell of a gene, a DNA or RNA sequence, a protein or an enzyme.

An "expression system" denotes a host cell and a compatible vector, which are used under suitable conditions to produce a protein encoded by an exogenous DNA carried by the vector and introduced into the host cell. Conventional expression systems include E. Coli host cells and plasmid vectors, insect cells and Baculovirus vectors, or mammalian cells and vectors with strong promoters of viral origin (for example cytomegalovirus).

The expression system according to the method of the invention is advantageously a bacterial expression system, in particular in E. Coli, with, for example, pGEX-4T-3 as vector. Bacterial systems are indeed the expression systems that generally allow the highest production yields to be obtained.

The invention therefore relates also to a method for producing a N protein-protein of interest fusion protein as defined above, which method comprises optionally the transformation of a host cell and then culturing the host cell transformed with a vector comprising a nucleic acid coding for the N protein-protein of interest fusion protein under conditions permitting the expression of N protein-protein of interest fusion proteins, and optionally the purification of the expressed N protein-protein of interest fusion proteins. The culture conditions depend on the selected expression system (that is to say host cell and vector) and the determination of those conditions is within the scope of the person skilled in the art.

Method for the Preparation of N Protein-Protein of Interest/P Protein Complex

The inventors have previously shown that the N protein of a virus of the Paramyxoviridae family can be produced in a coexpression system with the P protein of the same virus of the Paramyxoviridae family. The same system can be used to express the N protein-protein of interest fusion protein in the form of a complex with the P protein, and then optionally purify the fusion protein from that complex.

The invention relates to a method for the preparation of a N protein-protein of interest/P protein complex, the N and P proteins being proteins of a virus of the Paramyxoviridae family, said method comprising the steps consisting in:
a) coexpressing a N protein of a virus of the Paramyxoviridae family-protein of interest fusion protein, in which the protein of interest is fused in frame at the C-terminal end of the N protein, with a P protein of the same virus of the Paramyxoviridae family;
b) collecting the so formed N protein-protein of interest/P protein complexes.

As specified above, the N protein may carry, at its N-terminal end, a tag such as a histidine tag. Furthermore, the protein of interest may itself be a fusion construction.

In addition, as described above, the N protein may be a native N protein or may have been modified in the region defined by the last 25, preferably the last 20, 15, 10 or 5, C-terminal amino acids, provided that the modified N protein retains the ability to interact with the P protein. Such modifications typically consist in the deletion, substitution and/or insertion of one or more amino acids (for example from 1 to 25, or from 1 to 20, from 1 to 15, from 1 to 10, or alternatively from 1 to 5 contiguous or non-contiguous amino acids) in the C-terminal sequence of the N protein. An example of a sequence modification of the N protein can consist in a deletion of the 6 or 12 C-terminal amino acids, these truncated N proteins (NΔ6C and NΔ12C) still being capable of interacting with the P protein.

Preferably, said P protein is a truncated P protein ("PΔ") which does not contain the oligomerization domain P and which comprises a binding domain to the N protein. The inventors have indeed previously shown that this embodiment permitted the expression of a large quantity of N—P complexes in soluble form (patent application FR 05 04 426). The solubility is determined by centrifugation for 30 minutes at 10,000×g in respect of an aqueous medium, without detergent, for example a saline solution such as 1×PBS (NaCl 140 mM, KCl 27 mM, $Na_2HPO_4$ 8 mM, $KH_2PO_4$ 1.5 mM, pH 7.4) or a Tris buffer 10 mM pH 7.4, 150 mM NaCl.

The expression "truncated protein" denotes a P protein in which one or more contiguous amino acid sequences have been deleted. It may be the truncation of a C-terminal sequence, a N-terminal sequence, a sequence that is "internal" relative to the primary structure of the P protein, or a combination of these truncations.

The truncated P proteins according to the invention do not contain the oligomerization domain P and are capable of interacting with the N protein, that is to say they have a binding domain to the N protein. Since the domain of interaction of the Paramyxoviridae P protein with the N protein has been mapped in the region of the C-terminal end, examples of truncated P protein preferably include a C-terminal fragment of the P protein, or a "chimeric" P protein constituted by the fusion of a C-terminal fragment of the P protein (capable of interacting with the N protein) with at least one other sequence of contiguous amino acids of the P protein. Said C-terminal fragment and said other sequence of the P protein are not themselves naturally contiguous and do not exhibit sequence overlapping. For example, a truncated RSV P protein may have the sequence constituted by amino acids 1 to 121 and 161 to 241 of the native P protein. A "fragment" of a reference polypeptide denotes any sequence of contiguous amino acids found in the sequence of the reference polypeptide.

The expression "C-terminal fragment of the protein" or "PΔN" is understood as meaning a P protein in which one or more consecutive amino acids have been deleted starting from the N-terminal end. Preferably, a C-terminal fragment of the P protein denotes a chain of amino acids situated in the C-terminal half of the primary structure of the P protein (when the number of amino acids in the sequence is odd, an additional amino acid can be allocated arbitrarily to the C-terminal half of the protein relative to the N-terminal half). For example, in the case of the RSV P protein, which comprises 241 amino acids, PΔ161N denotes a C-terminal fragment constituted by amino acids 161 to 241 of the P protein. Also for example, in the case of the P protein of the measles virus (strain Edmonston B), which comprises 507 amino acids, PΔ386N denotes a C-terminal fragment constituted by amino acids 386 to 507 of the P protein.

When the truncated P protein is a C-terminal fragment of the P protein, the invention then relates to a method for the preparation of a soluble N protein-protein of interest/C-terminal fragment of the P protein complex ("N—PI/PΔN complex") of a virus of the Paramyxoviridae family, said method comprising the steps consisting in:
a) coexpressing a N protein of a virus of the Paramyxoviridae family, fused in frame at its C-terminal end with a protein of interest, with a C-terminal fragment of the P protein of the same virus of the Paramyxoviridae family, wherein said C-terminal fragment of the P protein does not contain the oligomerization domain P and is capable of interacting with the N protein-protein of interest fusion protein;
b) collecting the soluble N—PI/PΔN complexes so formed.

Said virus of the Paramyxoviridae family may be a Paramyxovirinae or Pneumovirinae. In particular, the virus may be selected from the group constituted by the mumps virus, the measles virus, the human Metapneumovirus, the parainfluenza virus and respiratory syncytial virus. Preferably, the virus is a Pneumovirus such as human or bovine respiratory syncytial virus (RSV).

The person skilled in the art knows, or is capable of determining, truncated P proteins, or more specifically C-terminal fragments of the P protein, which are capable of interacting with the antigen-N protein fusion protein.

For example, the strategy of coexpressing the N and P proteins in *E. Coli* described by Castagne et al. (2004, Journal of General Virology; 85: 1643-1653) may be used to map the interaction domain between P and N. The inventors have thus shown that C-terminal fragments of the RSV P protein, comprising an oligopeptide constituted by the 9 C-terminal amino acids of the P protein (amino acids 233 to 241), are capable of interacting with the N protein.

Moreover, it has been described, for example, that the interaction domain of the Sendai virus P protein with the N protein in the form of RNA-N complex or ribonucleoprotein (RNP), called the "X domain" or XD, is defined by amino acids 473 to 568 (Kolakofsky et al., 2004; Virology; 318(2): 463-73).

The inventors have also demonstrated that certain C-terminal fragments of the RSV P protein, especially fragment PΔ161N (amino acids 161 to 241), permitted the preparation of large quantities of N protein as compared with whole P protein which, in practice, does not permit to achieve sufficient yields on an industrial scale. The smaller deletion mutants, down to PΔ233N (amino acids 233 to 241), which contains only 9 amino acids, permit to achieve yields comparable with those of PΔ161N.

Those fragments smaller than PΔ161N correspond to fragments of the RSV protein that are capable of interacting with the N protein and which are no longer capable of oligomerization and therefore no longer contain the oligomerization domain P. The minimum oligomerization domain P of RSV would in fact be defined by amino acids 120 to 150 of the P protein.

That same strategy allowed the inventors to show that a C-terminal fragment of the P protein of the measles virus, constituted by amino acid residues 386-507 (PΔ386N), interacted with the N protein of that virus and permitted its purification. By contrast, a deletion of the N-terminal part of the P protein, as far as residue 456 (inclusive; fragment PΔ457N), does not permit purification of the N protein. The structure of the C-terminal region of the P protein that interacts with the ribonucleocapsid has been determined by Johansson et al. (2003 Journal of Biological Chemistry Vol. 278, p. 44567-44573). The oligomerization region P has been determined by deletion and prediction as being defined by amino acids 304-376.

The use of C-terminal fragments of the P protein which contain the interaction domain with the N protein in the form of RNP but in which the oligomerization domain P has been deleted therefore permits the interaction of the protein P fragments with the N protein, the formation of soluble N—PΔN complexes and the production of those complexes with a high yield. Without wishing to be limited to a particular mechanism, it is assumed that the absence of the oligomerization domain P avoids problems of insolubility of the N-ΔPN complexes associated with interactions between P proteins of those complexes.

Accordingly, according to an embodiment, the method for preparing N—PI—PΔN complex involves the expression of a C-terminal fragment of the RSV P protein which comprises the last 9 C-terminal amino acids of the RSV P protein and which is devoid of at least the 119, preferably the 149, more preferably the 160 N-terminal amino acids of the RSV P protein.

More specifically, in the method according to the invention it is possible to coexpress with the N protein-protein of interest fusion protein of RSV:

a) a C-terminal fragment of the RSV P protein which comprises the amino acid sequence 233 to 241 of the P protein of human RSV Long strain as shown in SEQ ID NO:1 and which extends in the N-terminal direction as far as an amino acid residue located between positions 233 and 120, preferably 150, more preferably 161, of the sequence of the RSV P protein as shown in SEQ ID NO:1, or b) a C-terminal fragment, the homolog of the fragment defined in a), of a P protein obtained from a different human RSV strain or from a bovine RSV strain.

The C-terminal fragment of the RSV P protein may be selected, for example, from the group constituted by PΔ120N (amino acids 120 to 241 of P), PΔ150N (amino acids 150 to 241 of P), PΔ161N (amino acids 161 to 241 of P), PΔ180N (amino acids 180 to 241 of P), PΔ200N (amino acids 200 to 241 of P), PΔ220N (amino acids 220 to 241 of P), PΔ230N (amino acids 230 to 241 of P) and PΔ233N (amino acids 233 to 241 of P).

The invention relates also to a method wherein there is coexpressed, with the N protein-protein of interest fusion protein of RSV, a truncated P protein comprising a C-terminal fragment of the RSV P protein as described above, which comprises the last 9 C-terminal amino acids of the RSV P protein and which is devoid of at least the 119, preferably the 149, more preferably the 160 N-terminal amino acids of the RSV P protein.

For example, the truncated P protein comprising a C-terminal fragment of the P protein may be constituted by the fusion of the last 122 N-terminal amino acids with the last 80 C-terminal amino acids of the RSV P protein; it may, for example, be constituted by the chain of amino acids 1 to 121 and 161 to 241 of the P protein of human RSV Long strain as shown in SEQ ID NO:7.

According to another embodiment, the Paramyxoviridae is the measles virus and the method for the preparation of N—PI—PΔN complex involves expressing a C-terminal fragment of the P protein of the measles virus comprising at most the 122 C-terminal amino acids of the P protein or being constituted thereby. In particular, it may be a C-terminal fragment constituted by acids 386 to 507 of the P protein (PΔ386N) of the measles virus strain Edmonston B, as shown in SEQ ID NO:10, or of a C-terminal fragment, homologous to that defined for the P protein of the strain Edmonston, of a P protein obtained from a different strain of the measles virus.

In the context of the invention, the term "homologous" relates to the relationship that exists between proteins having the same evolutive origin, for example homologous proteins belonging to different species, or, in the case of viruses, of viral strains. Such proteins (and the genes encoding them) have sequence homologies, reflected by their sequence similarities, whether it be in terms of percentage similarity or in terms of the presence of specific residues or motifs at conserved positions.

The expression "sequence similarity" denotes the degree of identity between sequences of nucleic acids or of amino acids of proteins which may or may not share the same evolutive origin. The terms homology and similarity are conventionally used indiscriminately. Two amino acid sequences are "substantially homologous" when their amino acids are at least 80% identical or at least 90% similar (that is to say functionally identical). Similar or homologous sequences can be identified by alignment using the programs BLAST or FASTA, for example.

Advantageously, the P protein, for example the truncated P protein and in particular the C-terminal fragment of the P protein, is expressed in the form of a fusion with a protein that facilitates the purification of the N protein-protein of interest/P protein complexes, especially a protein which can be used in affinity chromatography. It may be a protein tag, such as glutathione-S-transferase (GST), in which case the P protein-GST fusion protein can be isolated by chromatography on a solid support coupled with glutathione. Other labels or "tag", such as polyhistidine or "His-Tag", may be used.

There are thus obtained N protein-protein of interest/P protein-protein tag (GST or another protein tag fused with the P protein) complexes in which the protein tag can be removed by enzymatic cleavage. For example, GST may be removed by cleavage with thrombin or with any other suitable enzyme when the fusion comprises a protein other than GST.

Specific examples of the construction of vectors which allow the method according to the invention to be carried out are described in the examples below.

According to an embodiment, the protein of interest is an antigen and the method according to the invention results in the formation of soluble N protein-antigen/P protein complexes (N—Ag/P complex), preferably N protein-antigen/truncated P protein complexes (N—Ag/PΔ complex) and more preferably N protein-antigen/C-terminal fragment of the P protein complexes (N—Ag/PΔN).

Separation of the Fusion Proteins from the N Protein-Protein of Interest/P Protein Complexes The method for preparing a N protein-protein of interest/P protein complex, wherein the protein may be truncated and be in particular a C-terminal fragment of the P protein, as described above allows N protein-protein of interest/P protein complexes readily to be obtained in isolated or purified form.

The invention therefore relates also to a N protein-protein of interest/P protein complex, the N and P proteins being proteins of a virus of the Paramyxoviridae family, being obtainable by a preparation method as described above.

The invention relates in particular to a soluble N protein-protein of interest/truncated P protein complex (N—PI/PΔ complex) and more specifically to a soluble N protein-protein of interest/C-terminal fragment of the P protein complex (N—PI/PΔN complex), N and P being proteins of a virus of the Paramyxoviridae family.

Starting from those N protein-protein of interest/P protein complexes, or more specifically N—PI/PΔ or N—PI/PΔN, the N protein-protein of interest fusion protein can readily be isolated in the form of rings, with their RNA, for example by size exclusion chromatography (gel filtration). This separation may be carried out, where appropriate, after separation, by enzymatic cleavage of the P protein and the protein tag to which the protein is optionally fused.

The invention therefore relates further to a method for preparing N protein of a virus of the Paramyxoviridae family-protein of interest fusion proteins, said method comprising the steps consisting in:
a) preparing a N protein-protein of interest/P protein complex by a method as defined above; and
b) separating the N protein-protein of interest fusion proteins from the N protein-protein of interest/P protein complexes.

Preferably, the P protein is a truncated protein, more preferably a C-terminal fragment of the P protein.

The invention relates more particularly to a method for preparing soluble N protein-protein of interest of a virus of the Paramyxoviridae family fusion proteins, said method comprising the steps consisting in:

a) preparing a soluble N protein-protein of interest/C-terminal fragment of the P protein complex (N—PI/PΔN complex) by a method as defined above; and
b) separating the N protein-protein of interest fusion proteins from the soluble N—PI/PΔN complexes.

As described above, the N protein may be a native N protein or may have been modified in the region defined by the last 25, preferably the last 20, 15, 10 or 5, C-terminal amino acids, provided that the modified N protein retains the ability to interact with the P protein. Such modifications typically consist in the deletion, substitution and/or insertion of one or more amino acids (for example from 1 to 25, or from 1 to 20, from 1 to 15, from 1 to 10, or alternatively from 1 to 5 contiguous or non-contiguous amino acids) in the C-terminal sequence of the N protein. An example of a sequence modification of the N protein may consist in the deletion of the 6 or 12 C-terminal amino acids, those truncated N proteins (NΔ6C and NΔ12C) still being capable of interacting with the P protein.

The invention relates also to N protein-protein of interest fusion proteins obtainable by the above method.

The protein of interest may be a protein of therapeutic or vaccinal interest. Preferably, the protein of interest is an antigen.

Immunogenic, Vaccinal or Therapeutic Compositions

The inventors have previously shown that the RSV N protein having a ring-like structure, isolated or in the form of a N protein/C-terminal fragment of the P protein complex (N—PΔN), is highly immunogenic and especially permits the stimulation of a local response, for example in the respiratory mucosa.

The inventors have now demonstrated that those ring-like structures can be used as a vector for therapeutic or vaccinal proteins.

The invention therefore relates to the use of a N protein of a virus of the Paramyxoviridae family as a vector for molecules or proteins of therapeutic or vaccinal interest.

According to an embodiment, a therapeutic or vaccinal protein is fused to the N protein, as described above.

According to another embodiment, a therapeutic or vaccinal molecule is chemically coupled to the N protein. By adding a cysteine at the C-terminal end of the N protein there is in fact created a site which permits the chemical coupling of various molecules of proteic or non-proteic (organic or mineral) nature. It is possible to graft a protein also carrying a cysteine by a disulfide bridge. The maleimide itself coupled to various molecules can thus be grafted onto this cysteine by a covalent bond. The maleimide may be coupled to all kinds of organic molecules, such as dextrone, biotin, gold, or any protein.

The invention therefore relates also to a conjugate of the N protein of a virus of the Paramyxoviridae family with a molecule of interest, in particular a therapeutic or vaccinal molecule.

The invention relates also to a method for delivering a therapeutic or vaccinal molecule or protein to a subject, which method comprises delivering to said subject said therapeutic or vaccinal molecule covalently bonded to a N protein of a virus of the Paramyxoviridae family, or comprises delivering said protein in the form of a fusion protein with the N protein of a virus of the Paramyxoviridae family, the therapeutic or vaccinal protein being fused in frame at the C-terminal end of the N protein.

The invention also proposes a pharmaceutical composition comprising a N protein-protein of interest fusion protein, optionally in the form of a N protein-protein of interest/P protein complex, the N and P proteins being from the same virus of the Paramyxoviridae family, in a pharmaceutically acceptable carrier.

Said virus of the Paramyxoviridae family may be a Paramyxovirinae or Pneumovirinae. In particular, the virus may be selected from the group constituted by the mumps virus, the measles virus and the parainfluenza virus. Preferably, the virus is a Pneumovirus, in particular respiratory syncytial virus (RSV), for example human or bovine.

The protein of interest may be a protein of therapeutic or vaccinal interest.

According to an embodiment, the pharmaceutical composition is suitable for therapeutic use. According to this embodiment, the protein of interest is a protein of therapeutic interest. The inventors have demonstrated that the N protein-protein of interest fusion protein penetrates into the cells and that the N protein therefore constitutes a potential vector for molecules or proteins of therapeutic interest, such as, for example, an antiangiogenic or proapoptotic polypeptide.

According to an embodiment, the pharmaceutical composition is suitable for immunogenic or vaccinal use. According to this embodiment, the protein of interest is an antigenic protein, preferably an antigen derived from a pathogenic microorganism, such as a virus, a bacterium, a fungus or a parasitic metazoan or protozoan organism.

The inventors have in fact shown that the response of a host towards an antigen is very significantly increased when this antigen is presented in the form of a fusion protein with the N protein. The N protein-antigen fusion proteins are capable of stimulating the immune response by the cellular as well as the humoral route.

The soluble N protein-antigen fusion proteins can be used for vaccination in the form of a complex with the P protein without any adverse effect. Consequently, an immunogenic or vaccinal composition according to the invention may comprise a soluble N protein-antigen/P protein complex, in association with a pharmaceutically acceptable carrier.

"Pharmaceutically acceptable carrier" is understood as meaning any solvent, dispersion medium, absorption-retarding agent etc. that does not produce any side effect, for example an allergic reaction, in humans or animals.

Examples of physiologically acceptable carriers are known to the person skilled in the art. Examples of liquid carriers include sterile aqueous solutions which do not contain any material other than the active ingredients and water, or which contain a buffer such as sodium phosphate at physiological pH value, with a physiological salinity, or both, such as a phosphate-buffered saline solution (PBS). Aqueous carriers can contain more than one buffer salt as well as salts such as sodium or potassium chloride, dextrose, polyethylene glycol and other solutes.

The compositions are administered in a manner compatible with the galenical formulation and in a therapeutically effective amount. The amount to be administered depends on the subject to be treated, on the ability of the subject's system to use the active ingredient, and on the desired degree of therapeutic effect. The precise amounts of fusion protein required for the administration depend on the choice of the physician and on the particularities of each individual.

Advantageously, when the pharmaceutical composition is an immunogenic or vaccinal composition, it may further comprise an adjuvant. An "adjuvant" denotes a product which increases, stimulates, activates, improves or modulates the immune reaction at cell or humoral level directed against an antigen administered simultaneously. Examples of conventional adjuvants include adjuvants containing bacterial antigens, such as Freund's complete adjuvant, LPS and its derivatives, bacterial toxins (cholera toxin and enterotoxin) and their detoxified mutants (for example LT(R192G)), oligonucleotide sequences containing CpG motifs, mineral adjuvants such as aluminium hydroxide (alum), calcium phosphate or potassium phosphate, oily emulsions and emulsifying agents (saponins, for example QS21), cytokines.

The immunogenic compositions according to the invention allow an immune response to be induced against the antigen in the vaccinated subject, or more specifically against the pathogen from which the antigen is derived.

The vaccinal compositions according to the invention allow protection to be conferred against an infection by a pathogen comprising the antigen, that is to say a reduction in the severity of the effects of such an infection as compared with a subject which has not been immunized with the vaccinal composition.

The invention relates also to the use of a vaccinal composition as defined above in a method of vaccination against the pathogen from which the antigen is derived.

The invention therefore relates to a vaccination method comprising at least one administration of a vaccinal composition according to the invention to a subject. Preferably, the vaccination method comprises a first administration to a subject of a vaccinal composition and at least one booster administration of said vaccinal composition to the same subject. The booster administrations, by reexposing the patient to the antigen, induce a stronger secondary immune response.

The vaccinal composition is advantageously administered in an amount that is effective in inducing a protective or therapeutic immune response to an infection by the pathogen from which the antigen is derived. The dosage naturally depends on the active ingredient in question, on the mode of administration, and on the age and condition of the subject. The amount of N—Ag—P, N—Ag—PΔ or N—Ag—PΔN complex or of N—Ag fusion protein per dose can be from 0.1 to 200 µg, preferably from 10 to 100 µg, per vaccinal dose.

The immunogenic, vaccinal, or pharmaceutical composition can be administered by any route, in particular by the mucosal (for example ocular, intranasal, oral) route or by the parenteral (for example subcutaneous, intradermal, intramuscular, intravenous or intraperitoneal) route.

The expression "subject" denotes a human being or a non-human animal, for example a bird or a mammal such as a bovine, an ovine, a rodent, a canine, in particular a dog, a feline, in particular a cat, a pig, a monkey, which has been exposed or is likely to be exposed to an infection by a Paramyxoviridae virus or by any other pathology. A subject within the scope of the invention is preferably a human being or a bovine.

For each of those aspects, and as described above, the N protein may be a native N protein or may have been modified in the region defined by the last 25, preferably the last 20, 15, 10 or 5, C-terminal amino acids, provided that the modified N protein retains the ability to interact with the P protein. Such modifications typically consist in the deletion, substitution and/or insertion of one or more amino acids (for example from 1 to 25, or from 1 to 20, from 1 to 15, from 1 to 10, or alternatively from 1 to 5 contiguous or non-contiguous amino acids) in the C-terminal sequence of the N protein. An example of a sequence modification of the N protein may consist in the deletion of the 6 or 12 C-terminal amino acids, those truncated N proteins (NΔ6C and NΔ12C) still being capable of interacting with the P protein.

Diagnostic Applications

The fusion of an antigen comprising at least one epitope with the N protein of a Paramyxoviridae virus additionally constitutes a reagent likely to be used in diagnostic applications for detecting antibodies directed against at least one of said epitopes carried by the fusion protein.

The invention therefore relates further to a diagnostic reagent comprising a N protein-antigen fusion protein comprising an antigen fused in frame at the C-terminal end of a N protein of a virus of the Paramyxoviridae family, as described above.

A diagnostic kit comprising said reagent and appropriate detection means are likewise within the scope of the invention.

Said antigen comprises at least one epitope and may likewise comprise two or more than two identical or different epitopes.

The invention also proposes the use of a N protein-antigen fusion protein for the detection, in vitro or in vivo, of antibodies directed against said antigen of the fusion protein.

When the antigen comprises a single epitope, the detected antibodies are then specific for that epitope.

When the antigen comprises two or more than two different epitopes, the detected antibodies can be specific for one, two or more than two of the epitopes of said antigen.

The invention relates also to a method for detecting, in a biological sample, antibodies specific for an antigen, which method comprises the steps consisting in:
a) contacting said biological sample with a N-antigen fusion protein comprising an antigen fused in frame at the C-terminal end of a N protein of a virus of the Paramyxoviridae family,
b) detecting the resulting N-antigen fusion protein/antibody complexes,
the presence of such complexes being indicative of the presence of antibodies specific for the antigen in the biological sample.

The biological sample may be a tissue sample obtained, for example, by muscular, hepatic, cardiac, cerebral, etc. biopsy, or a liquid sample, for example a biological liquid such as blood, plasma or cerebrospinal fluid.

The detection of the complexes may be carried out by conventional means well known to the person skilled in the art, such as chromatography (size exclusion, affinity, etc.) or electrophoresis under non-denaturing conditions.

The detection of the N-antigen/antibody complexes may additionally be facilitated by labelling the N proteins in a detectable manner.

For each of those aspects, the N protein may be a native N protein or may have been modified in the region defined by the last 25, preferably the last 20, 15, 10 or 5, C-terminal amino acids, provided that the modified N protein retains the ability to interact with the P protein. Such modifications typically consist in the deletion, substitution and/or insertion of one or more amino acids (for example from 1 to 25, or from 1 to 20, from 1 to 15, from 1 to 10, or alternatively from 1 to 5 contiguous or non-contiguous amino acids) in the C-terminal sequence of the N protein. An example of a sequence modification of the N protein may consist in the deletion of the 6 or 12 C-terminal amino acids, those truncated N proteins (NΔ6C and NΔ12C) still being capable of interacting with the P protein.

The following examples and figures illustrate the invention without limiting the scope thereof.

FIGURES

FIG. 1 shows the capture of the N-GFP—PΔN complexes by HEp2 or RAW cells. The HEp-2 (A; C) or RAW (B; D) cells were incubated in the presence of DX-FITC (A; B) or N-GFP—PΔN (C; D). The incubation lasted one hour at 4° C. (curves in dotted lines) or two hours at 4° C. (curves in continuous bold lines) or one hour at 37° C. (curves in continuous lines) or two hours at 37° C. (curves in dotted bold lines). The fluorescence (FITC or GFP) was analyzed by flow cytometry on 100,000 events.

Figure 2:
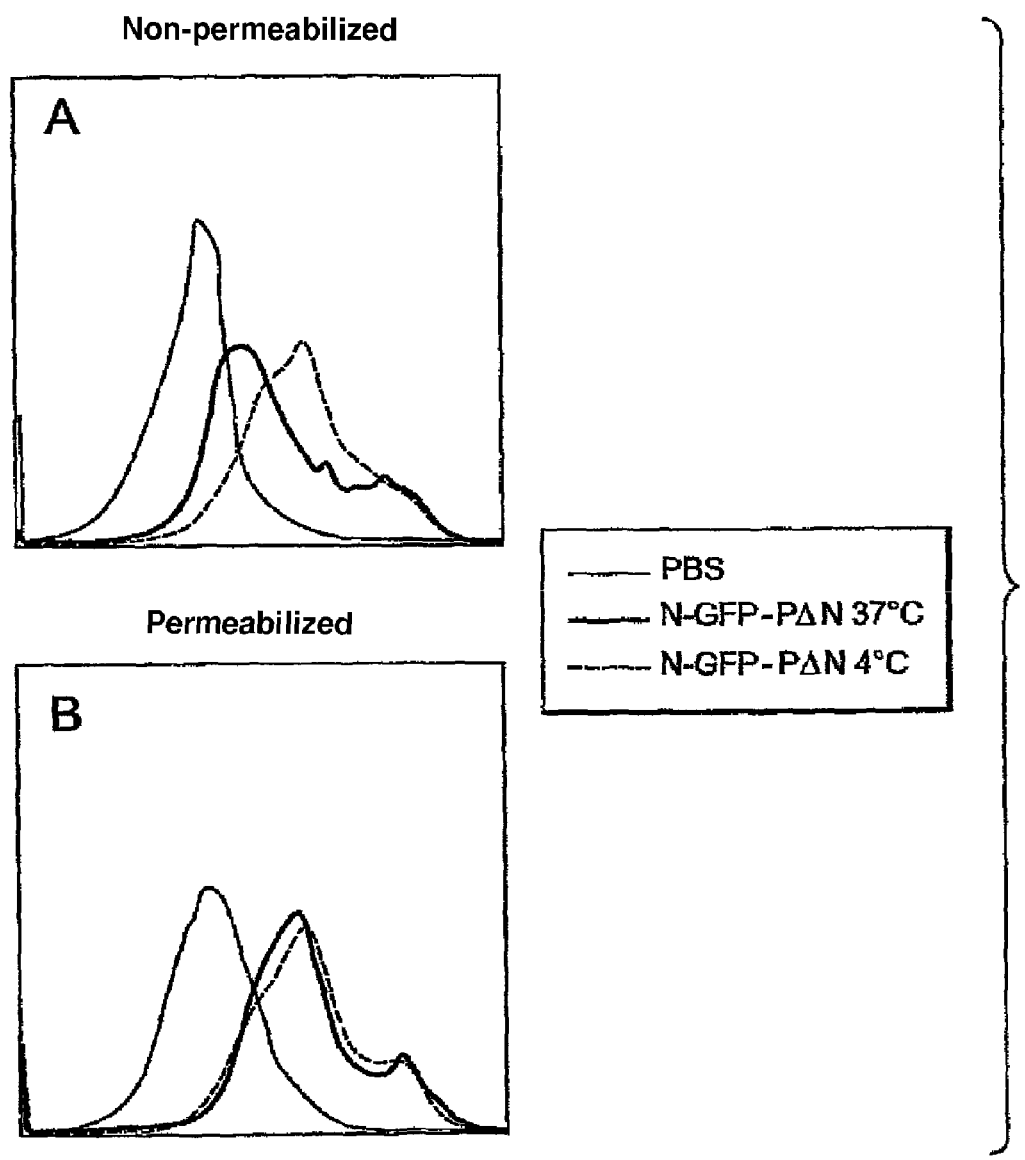

FIG. 2 shows that the N-GFP—PΔN complexes are internalized in the RAW cells. The RAW cells were incubated for one hour in the presence of N-GFP—PΔN at 4° C. (curves in continuous bold lines) or at 37° C. (curves in dotted lines). The N protein was detected by indirect immunolabeling by flow cytometry on non-permeabilized cells (A) or permeabilized cells (B). The autofluorescence of the cells was given by the signal of the cells incubated at 37° C. in PBS (curves in continuous lines).

Figure 3:
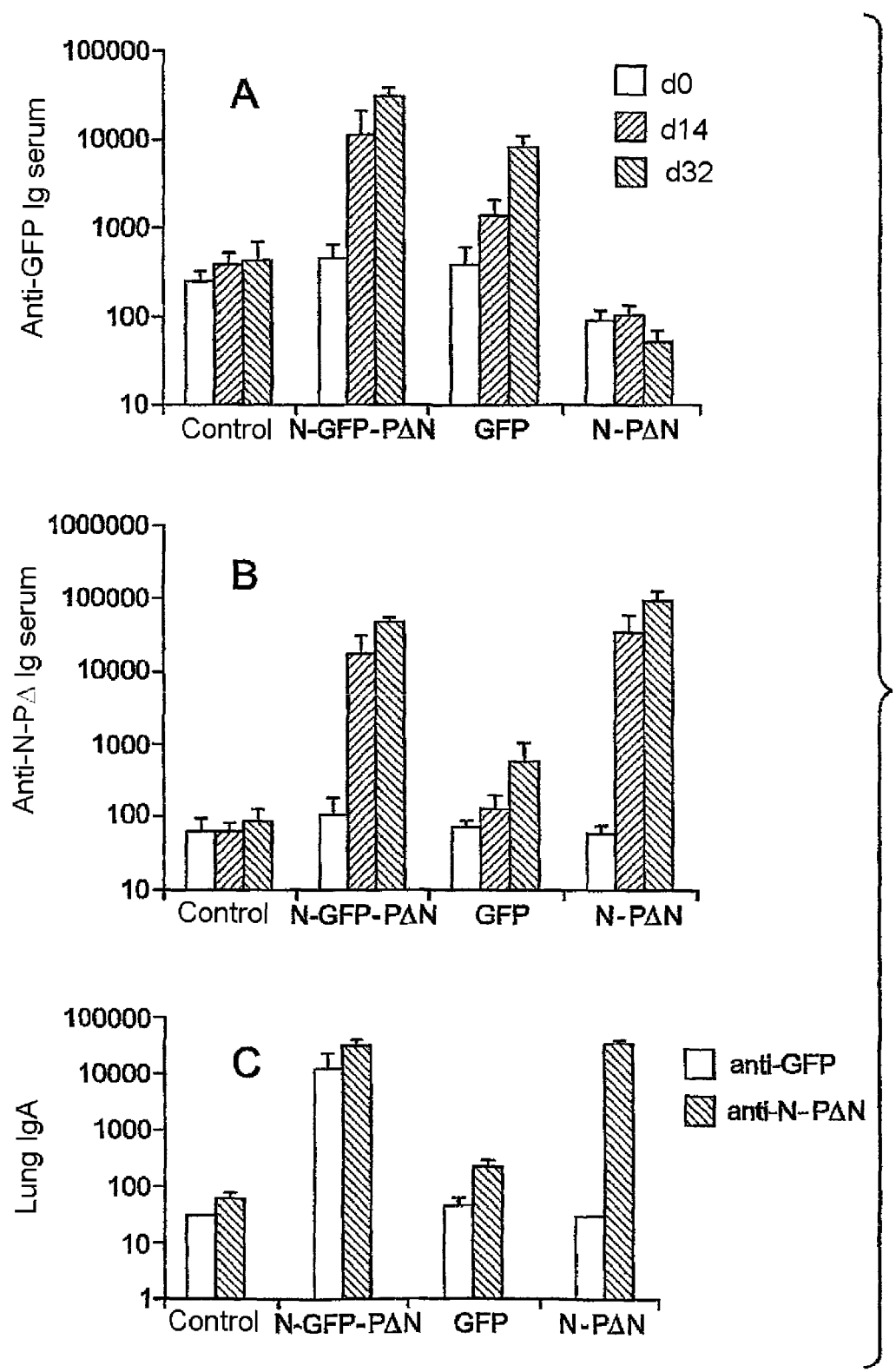

FIG. 3 shows the increase in the antibody response by vectorization of GFP on the N—PΔN complexes. BALB/c mice were immunized on day d0, by the nasal route, with the adjuvant alone (control), the N-GFP—PΔN complex, N—PΔN or GFP, still in the presence of adjuvant. A booster injection was carried out after two weeks (d14). The animals were sacrifized two weeks after the booster injection (d28). The serum was collected on d0, d14 and d28 (A and B). Bronchoalveolar washing was carried out on d28 (C). The titer of anti-N—PΔN antibodies (B and C) and anti-GFP antibodies (A and C) was determined by ELISA. The data were expressed as the mean±standard error of the mean (n=8 for the control and GFP groups, n=6 for the N-GFP—PΔ group, n=4 for the N—PΔ group) and were represented according to a logarithmic scale.

Figure 4:
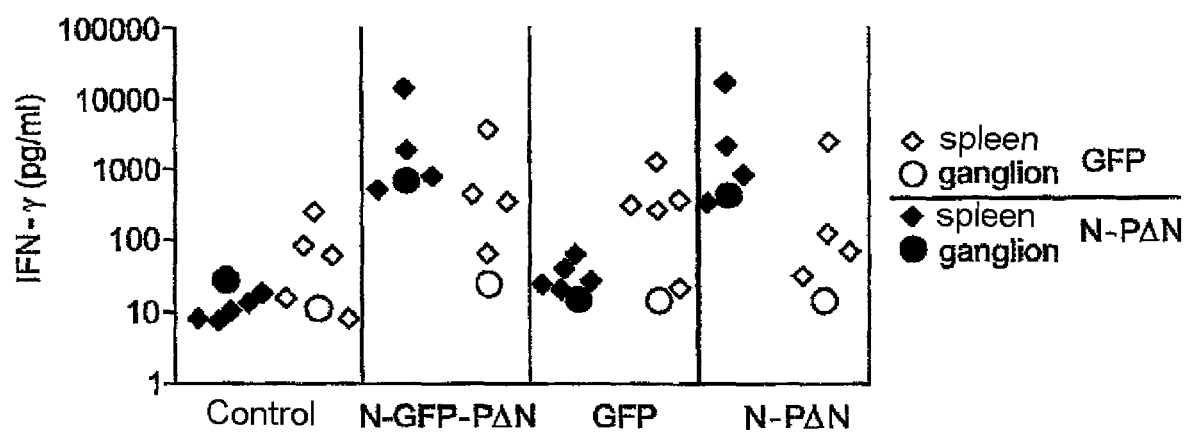

FIG. 4 shows the absence of memory T response against GFP, including in its form vectorized by N—PΔN. BALB/c mice were immunized on day d0, by the nasal route, with the adjuvant alone (control), the N-GFP—PΔN, N—PΔN complexes or GFP, still in the presence of adjuvant. A booster injection was carried out after two weeks (d14). The animals were autopsied two weeks after the booster injection (d28) in order to remove the spleens and the locoregional ganglions. The cell suspensions were treated individually for the spleens (diamonds) and in a pool per group for the ganglions (circles). The cells were restimulated for 72 hours with GFP (white diamonds and circles) or N—PΔN (black diamonds and circles). The secretion of IFN-γ was measured by ELISA. When the cells were cultured in medium alone, the basal level of IFN-γ was less than 15 µg/ml.

EXAMPLES

Example 1

Construction of Plasmids Containing the C-Terminal Region of RSV Phosphoprotein and RSV N Protein Fused to GFP The P protein of RSV Long strain is composed of 241 amino acid residues.

Sequences of the oligonucleotide primers (from 5' to 3') used to amplify the C-terminal portion of the RSV P protein (the BamHI restriction sites are underlined; the start codon ATG of the P gene is shown in bold letters):

```
LONG-PBam+:
                                      (SEQ ID NO: 13)
GAGGGATCCATCATGGAAAAGTTTGCTCCTG

LONG-P-:
                                      (SEQ ID NO: 14)
CTGTTGGTGTTGTGTGTTGAAGTGCAG

P161B+:
                                      (SEQ ID NO: 15)
GAGGGATCCTCTGCTAGGGATGGTATAAGAG

P180B+:
                                      (SEQ ID NO: 16)
GAGGGATCCAAAATCAGAACTGAAGCATTAATGACC

P201B+:
                                      (SEQ ID NO: 17)
GAGGGATCCGAGGAAAGTGAAAAGATGGCAAAAG

P221B+:
                                      (SEQ ID NO: 18)
GAGGGATCCGAGAAATTGAACAACCTGTTGG

P230NB+:
                                      (SEQ ID NO: 19)
GATCCAATGATAGTGACAATGATCTATCACTTGAAGATTTCTGA

P230N-:
                                      (SEQ ID NO: 20)
TCAGAAATCTTCAAGTGATAGATCATTGTCACTATCATTG
```

The cDNA of the P gene of RSV Long strain was amplified by RT-PCR starting from Hep-2 cells infected by the Long strain of human RSV using the primers LONG-PBam+ and LONG-P– (Castagné et al., 2004; Journal of General Virology; 85: 1643-1653). The PCR product was digested by the restriction enzyme BamHI and cloned into the plasmid pGEX-4T-3 (Pharmacia) at the BamHI-SamI sites in frame with the gene encoding glutathione-S-transferase or GST. The plasmid is called pGEX-P.

Cloning of P161-241 (PΔ161N)

The C-terminal region of P (amino acids 161-241) was amplified by PCR starting from the pGEX-P plasmid under the following conditions:
PCR primers: P161B+ and LONG-P— 100 ng each (1 μl each)
DNA template pGEX-P: 10 ng (1 μl)
Enzyme: Pfu Turbo™ Stratagene (2.5 Upper μl): 1 μl
dATP: 0.2 mM final
dGTP: 0.2 mM final
dCTP: 0.2 mM final
dTTP: 0.2 mM final
Pfu buffer 1× final (Stratagene)
Final volume: 100 μl The PCR was carried out under the following conditions:
5 cycles: 15 seconds at 94° C., 2 minutes at 40° C., 1 minute at 72° C.;
25 cycles: 15 seconds at 94° C., 1 minute at 55° C., 1 minute at 72° C.

The amplified DNA was extracted with one volume (100 μl) of phenol/chloroform (1 vol/1 vol) and then with one volume of chloroform and was finally precipitated by addition of one tenth of a volume of 5M NaCl (10 μl) and two volumes of 100% ethanol (200 μl). DNA was centrifuged for 20 minutes at 13,000 g, washed with one volume of 70% ethanol, dried, resuspended in one volume of water of 90 μl. After addition of 10 μl of 10× buffer for the enzyme BamHI, the DNA was digested for 2 hours at 37° C. in the presence of 10 units of enzyme BamHI. The digested DNA was deposited on a 1.5% agarose gel in 1× Tris-borate-EDTA buffer (TBE) in the presence of ethidium bromide and was made to migrate by electrophoresis. The band corresponding to the DNA of P161-241 was cut and the DNA was extracted by electroelution. It was extracted again with one volume of phenol-chloroform, one volume of chloroform and precipitated with ethanol. It was ligated with the vector pGEX-4T-3 digested by BamHI and SmaI after purification on 1% agarose gel:
pGEX4T-3 DNA: 100 ng
P161-241 DNA: 100 ng
ligase buffer 1× final
Ligase (5 U/μl): 1 μl
Final volume 20 μl The whole was incubated overnight at 14° C. On the following day, competent DH5-alpha TM bacteria (Life Technologies) were transformed with 10 μl of ligation product and spread on Petri dishes containing LB-agar medium supplemented with 100 μg/ml of ampicillin final. The recombinant bacterial colonies were screened by mini-plasmid preparation and digestion by the restriction enzymes BamHI and XhoI. The recombinant plasmids then show two bands in agarose gel, one corresponding to the vector (4.9 kb) and the second corresponding to the C-terminal part of P (246 pb). The recombinant plasmids were completely sequenced.

Cloning of P180-241, P201-241, P221-241

The fragments of P corresponding to the parts of amino acids 180-241, 200-241, 220-241 were obtained by PCR starting from the pGEX-P plasmid using the following primers:
P180-241: primers P180B+ and LONG-P
P200-241: primers P201B+ and LONG-P–
P220-241: primers P221B+ and LONG-P–

They were amplified and cloned in the same manner as P161-241 (see above).

Cloning of the Gene Encoding the Nucleocapsid Protein of RSV Long Strain

The gene encoding the N protein of human RSV Long strain was obtained by RT-PCR starting from Hep-2 cells infected by that virus. The primers used were:

```
LONG-Nbam+:
                                      (SEQ ID NO: 21)
GAGGGATCCATGGCTCTTAGCAAAGTCAAGTTG LONG-N-:
                                      (SEQ ID NO: 22).
TTAACTCAAAGCTCTACATCATTATCTTTTGG.
```

The PCR products were digested by BamHI and cloned in the pGEX-4T-3 plasmid at the BamHI-SmaI sites. The region encoding N was subcloned by digestion of the pGEX-N plasmid by BamHI-XhoI and subcloned in the pET28a+ plasmid (Novagen).

Mutagenesis of the pET-N Plasmid and Creation of a Unique SalI Restriction Site Upstream of the STOP Codon A SacI restriction site was introduced just before the stop codon of the N protein of human RSV (long strain) by directed mutagenesis using the following oligonucleotides:

```
Nfinsac+:
                                      (SEQ ID NO: 23)
CCAAAAGATAATGATGTAGAGCTCTGACTCGAGCACCACCACC Nfinsac-:
                                      (SEQ ID NO: 24)
GGTGGTGGTGCTCGAGTCAGAGCTCTACATCATTATCTTTTGG.
```

This allowed to obtain the pET-N-Sac plasmid.

Obtaining the N Protein Fused to GFP

GFP was removed from the pEGFPN1 plasmid by digestion by the restriction enzyme EagI and then Klenow treatment in the presence of nucleotides in order to obtain blunt ends on DNA, then digested by SacI. Plasmid pET-N-Sac was digested with the enzyme XhoI, treated with Klenow in the presence of nucleotides and then digested with SaI. GFP was thus inserted into the pET-N-Sac plasmid and allowed pET-N-GFP plasmid to be obtained.

Obtaining the N Protein-F Epitopes

"Mimotope" and "heptad" epitopes of the F protein of RSV were cloned at the C-terminal end of the N protein by insertion of double-stranded oligonucleotides.

```
Mimotope epitope:
F-Flag-HWSISKPQ+:
                                        (SEQ ID NO: 25)
CATGGACTACAAGGACGACGATGACAAGCACTGGTCTATCTCTAAACCGC
AGTAG F-Flag-HWSISKPQ-:
                                        (SEQ ID NO: 26)
TCGACTACTGCGGTTTAGAGATAGACCAGTGCTTGTCATCGTCGTCCTTG
TAGTCCATGAGCT
```

These mutually hybridized oligonucleotides were inserted at sites SacI-SalI in the pET-N-GFP plasmid.

Heptad Epitope:

The following oligonucleotides were hybridized together:

```
FheptadAge+:
                                        (SEQ ID NO: 27)
CCGGTCTCTACTAACAAAGCTGTTGTTTCTCTGAGCTAGT (SEQ ID NO: 28)
(STNKAVVSLS)

FheptadAge-:
                                        (SEQ ID NO: 29)
CCGGACTAGCTCAGAGAAACAACAGCTTTGTTAGTAGAGA
```

They were cloned at site AgeI in the pET-N-GFP plasmid.

Cloning of P231-241

The following primers were denatured by heating at 94° C. for 5 minutes and then cooled to room temperature:

```
P231NB+:
                                        (SEQ ID NO: 30)
GATCCGATAGTGACAATGATCTATCACTTGAAGATTTCTGA

P231 N-:
                                        (SEQ ID NO: 31)
TCAGAAATCTTCAAGTGATAGATCATTGTCACTATCG
```

After hybridization, 10 ng of double-stranded oligonucleotides were ligated with 100 ng of DNA of pGEX-4T-3 plasmid digested by the enzyme BamHI and SmaI and purified by agarose gel electrophoresis. The recombinant plasmids were verified by sequencing in the region of the N gene.

Example 2

Expression and Purification of the Complexes

Competent BL21 (DE3) bacteria (Novagen) were transformed with 1 µg of PGEX-PΔ DNA and 1 µg of pET-N DNA and then spread out on Petri dishes containing LB-agar medium supplemented with 100 µg/ml final of ampicillin and 50 µg/ml final of kanamycin. A colony was selected and cultured overnight at 37° C. in 2 ml of LB medium containing ampicillin and kanamycin in concentrations of 100 µg/ml and 50 µg/ml, respectively. On the following day, 1 ml of saturated culture was used to inoculate 1 liter of LB medium supplemented with antibiotics, and was cultured until the evening. In the evening, one volume of fresh LB medium containing IPTG (which induces the expression of the proteins) in a concentration of 160 µg/ml was added to the culture and the whole was cultured overnight at 28° C. On the following day, the bacteria were centrifuged for 15 minutes at 5000 rpm and the pellet was resuspended in 100 ml of the following buffer:

50 mM Tris pH 7.8
60 mM NaCl
2 mM DTT
1 mM EDTA
4 mM benzamidine
1× antiproteases (complete EDTA-free protease inhibitor cocktail, ref. Roche no. 11 873 580 001) namely one tablet for 50 ml of lysis buffer
0.1% Triton-X100

10 ml of the same buffer, supplemented with lysozyme in an amount of 10 mg/ml (1 mg/ml final), were added. The bacteria were incubated for 1 hour on ice (lysis). When the whole became viscous, the whole was sonicated 3 times for 1 minute using a probe immersed in the mixture, on ice, allowing 5 minutes' rest between each sonication. The whole was centrifuged for 30 minutes at 10,000 g at 4° C. and then the supernatant was recovered. The supernatant was centrifuged again for 30 minutes at 10,000 g at 4° C. and then the new supernatant was recovered. 4 ml of sepharose 4B-glutathione beads (Amersham-Pharmacia) were washed by removing 8 ml of beads/buffer mixture (vol/vol) with the lysis buffer. The beads were left in an equivalent volume of buffer, added to the clarified bacterial lysate and rotated at 4° C. overnight. On the following day, the beads were centrifuged at 2000 rpm for 3 minutes and then the supernatant was removed and the beads were washed three times with the lysis buffer without antiproteases, three times in 1×PBS buffer.

The beads were cleaved at the thrombin site using biotinylated thrombin (Novagen) in an amount of 1 µl (1 U) of thrombin ("Thrombin Cleavage Capture Kit", Novagen No. 69022-3FRZ) for 1 ml of beads. The beads were incubated overnight at 20° C. and on the following day were centrifuged for 3 minutes at 2000 rpm and allowed to decant for 15 minutes in order to collect the supernatant. An equivalent volume of 1×PBS was added to the beads; the mixture was stirred and decanted. The supernatant was again collected and added to the supernatant collected previously. To the collected supernatant there were added streptavidin-agarose beads (Novagen ref. 69023) in an amount of 16 µl of resin (that is to say 32 µl of resin/buffer mixture (vol/vol)). The mixture was stirred for one hour and then centrifuged for 3 minutes at 2000 rpm, and the supernatant was collected. A protein concentration of 2 mg/ml was obtained.

10 µl of the supernatant containing the cleavage products were denatured in 1× Laemmli buffer and then boiled and deposited on a 12% polyacrylamide gel in 0.1% Tris-glycine SDS buffer and then stained with Coomassie blue after electrophoresis in order to reveal the proteins.

Example 3

Separation of N-GFP and PΔ161N (P161-241) and Purification of the N-GFP Rings

The proteins present in the supernatant may be separated by size exclusion chromatography (gel filtration) in 1×PBS.

Example 4

Capture of the N—PΔN Complexes by Different Cell Lines: Study with the Aid of the N-Green Fluorescent Protein (GFP) Fusion Protein I. Material and Methods
I.1 Cell Lines and Phagocytosis Tests:
  HEp-2: human laryngeal epithelial line (Cancer Res 1955; 15:598), cultured in a monolayer in EMEM (Eagle's Minimum Essential Medium)+10% FCS+L-glutamine+ PS (penicillin, streptomycin).
  RAW: murine peritoneal monocyte-macrophage line (J. Immunol. 1977; 119:950) cultured in a monolayer in DMEM (Dulbecco's Minimum Essential Medium)+ 10% FCS+L-glutamine+PS.

The cell lines were dissociated in D-PBS (Dulbecco's Phosphate Buffered Saline)+0.33% lidocaine+5 mM EDTA. The isolated cells were washed, resuspended in a concentration of $10^7$ cells/ml in PBS+2% FCS and incubated, with gentle stirring, in 5 ml round-bottomed tubes in the presence of:
  P161-241+N-GFP(N-GFP—PΔN) at 20 µg/ml
  GFP at 6.5 µg/ml
  Dextran-FITC (DX-FITC) at 1 mg/ml (Ref: D-1844, Molecular Probes).

The incubations were carried out in parallel at 4° C., the temperature at which the endocytosis mechanisms are inhibited, and at 37° C., the permissive temperature for internalization. After incubation for one hour or two hours, the cells were washed three times and resuspended in PBS+2% FCS.

I.2 Analysis of Adsorption/Internalization by Flow Cytometry

The fluorescence (FL1) associated with the cells (HEp-2, RAW) incubated with fluorescent molecules (DX-FITC or N-GFP—PΔN) at 4° C. or 37° C. were compared by flow cytometry (FACSCalibur, Becton). The level of autofluorescence of the cells was given by cells incubated for two hours at 37° C. in the absence of fluorescent molecules.

I.3 Analysis of Adsorption/Internalization by Fluorescence Microscopy

After incubation, $10^5$ cells were deposited by cytocentrifugation on superfrost plus slides (SFPLUS-42, Milian). The slides were dried for 15 minutes and mounted in PERTEX (Ref: 00814, Histolab).

The level of fluorescence was observed with a microscope (Axiovert200M, Zeiss). Pictures were taken with a camera (Coolsnap HQ) using Metavue software.

I.4 Immunodetection of the N Protein After Permeabilization of the Cells

The object was to compare, by immunodetection of the N protein, the signal detected on the non-permeabilized cells (extracellular N-GFP—PΔN complex) with the signal detected on permeabilized cells (intra- and extra-cellular N-GFP—PΔN complex).

The cells were fixed for 15 minutes in A buffer (Ref: GAS-003, Caltag) and washed.

In the case of the non-permeabilized cells, labelling was carried out in Cell Wash buffer (Becton)+5% FCS. In order to permeabilize the cells during labelling, buffer B (Ref: RGAS-003, Caltag) was used. The Fc receptors were saturated for 20 minutes with an anti-CD16/CD32 antibody (Ref: 553141, Becton) diluted to 1/100. The cells were then incubated for 30 minutes with a rabbit serum directed against the N protein, diluted to 1/1000. Detection of the rabbit Ig was performed by incubation for 30 minutes with a biotinylated antibody (Ref: BA-1000, Vector) diluted to 1/200. The use of APC-coupled streptavidin (554067, Becton) at 1/500 permitted the indirect detection on the FL4 channel of the N protein by flow cytometry (FACSCalibur, Becton).

II. Results:
II-1 Analysis of the Interaction of the N-GFP—PΔN Complexes with the RAW Cells (Macrophages) and HEp2 Cells (Epithelial):

The RAW cells are a line of monocytes/macrophages. They have a phagocytosis capacity which can be observed by contacting them with a fluorescent polymer, DX-FITC. The capture of DX-FITC was greatly increased at 37° C. as compared with 4° C. (FIG. 1B). The HEp-2 line is an epithelial line. It does not have a capacity for phagocytosis, which is why the fluorescence linked with the interaction between DX-FITC and those cells is not very different between incubations at 4° C. and at 37° C. (FIG. 1A).

When the N-GFP—PΔN complexes were contacted with the RAW and HEp-2 cells, a considerable increase in the level of fluorescence relative to the basal level (PBS) was observed (FIG. 1 C, D). This indicated effective adsorption at the membrane of those cells. After incubation at 37° C., the fluorescence detected in the presence of N-GFP—PΔN diminished in both cell types but nevertheless remained superior to the basal level (FIG. 1 C, D). When the cells were incubated with recombinant GFP, the fluorescent signal remained at the basal level (data not shown). This indicated that the observed capture phenomena were associated with the N—PΔN rings and not with GFP.

The capture of the N-GFP—PΔN rings in the RAW and HEp-2 lines has been confirmed by microscopy.

The fluorescence specific to GFP fused to the N protein was found in the form of granules inside the HEp-2 or RAW cells. That fluorescence was not found in the case where the incubation was carried out with recombinant GFP. The N-GFP—PΔN complexes were therefore adsorbed and/or internalized in the RAW macrophage line and in the HEp-2 epithelial line.

II.2 Internalization of the N-GFP—PΔN Complexes by the RAW Cells

In order to understand the fate of the N-GFP—PΔN complexes in the RAW cells at 37° C. versus 4° C., the cells were permeabilized and the presence of the N protein was revealed by immunolabeling and analysis by flow cytometry (FIG. 2). In the absence of permeabilization, the amount of N detected (fluorescence signal) was smaller at 37° C. than at 4° C. (FIG. 2A). After permeabilization, on the other hand, the level of the signal became identical for the incubation conditions of 37° C. and 4° C. (FIG. 2B). The N-GFP—PΔN complexes were therefore internalized on incubation at 37° C.

In conclusion, the totality of the experiments carried out with the N-GFP—PΔN complexes, by flow cytometry and by microscopy, has made it possible to demonstrate the novel properties of these protein structures. The ring-like assemblies of the nucleoprotein have the ability to be adsorbed and internalized effectively by various cell types such as macrophages, epithelial cells and dendritic cells (data not shown). Those properties are particularly valuable for the use of these structures as an antigen vector for vaccination.

Example 5

Evaluation of the Antigen Vector Properties of the N Protein in Ring Form as Compared with Green Fluorescent Protein (GFP) Expressed in Fusion I. Material and Methods
I.1 Mice:
  Female BALB/c aged 8-10 weeks, reared at the Unité Experimentale Animalerie Rongeur (INRA, Jouy-en-Josas).

I.2 Antigens:
P161-241+N-GFP(N-GFP—PΔN) concentration at 0.1064 µg/µl
GFP concentration at 0.5 µg/µl
P161-241+N(N—PΔN) concentration at 1 µg/µl I.3 Adjuvant:
LT(R192G) detoxified lymphotoxin of *E. coli*, 1 mg/ml (batch sent by John Clements; Choi et al., 2004, Protein Expression and Purification 38, pp. 205).

I.4 Immunization:
Administration by the intranasal route (i.n.), under avertin anesthesia (300 □l i.p.), of the following mixture (60 µl/mouse)
5 µg of LT(R192G)
5 µg of N-GFP—PΔN
or 1.7 µg of soluble GFP
or 3.3 µg of N—PΔN
(amounts of GFP or of N—PΔN corresponding to those present in 5 µg of N-GFP—PΔN)
qsp 60 µl with apyrogenic physiological serum
All the solutions are passed through a 0.22 µm filter prior to injection.

| Groups | d0 Primo-injection | d14 booster | d32 autopsy |
|---|---|---|---|
| control | LT(R192G) i.n. serum | LT(R192G) i.n. serum | Serum Spleen BAW Draining gg |
| GFP | GFP + LT(R192G) i.n. serum | GFP + LT(R192G) i.n. serum | Serum Spleen BAW draining gg |
| N-PΔN | N-PΔN + LT(R192G) i.n. serum | N-PΔN + LT(R192G) i.n. serum | Serum Spleen BAW draining gg |
| N-GFP-PΔN | NGFP-PΔN + LT(R192G) i.n. serum | NGFP-PΔN + LT(R192G) i.n. serum | Serum Spleen BAW draining gg |

BAW: bronchoalveolar washing (with 1 ml of PBS 1 mM EDTA)
gg: ganglions

I.5 Production of Anti-N—PΔN and Anti-GFP Antibodies:
The anti-N—PΔN or anti-GFP antibodies (IgH+L and IgA) were searched in the serums and the BAW by ELISA:
The serums were collected from blood samples (1 night's exudation at 4° C.) and then frozen at −20° C.
The BAWs were centrifuged for 5 minutes at 1700 rpm, the supernatants were collected (approximately 1 ml) and frozen at −20° C.
96-well plates (Immulon 2HB, ThermoLabsystems) were sensitized for one night at 4° C. with the N—PΔN complex or the recombinant GFP protein (200 ng per well, 100 µl per well) in 0.1 M bicarbonate buffer, pH 9.5. The plates were washed 5 times with 200 µl per well of 0.05% PBS-Tween 20 (use of a Wellwash device, Labsystems). The plates were then saturated for 1 hour at 37° C. with 150 µl per well of 0.05% PBS-Tween 20 buffer and 5% fetal calf serum (PBS-T-FCS). After 5 washes, the samples to be titrated were diluted in PBS-T-FCS (seven successive dilutions with a factor of 3 starting from a first dilution to ⅟30th for the serums and to one third for the BAWs). The plates were incubated for 2 hours at 37° C. After 5 washes, the secondary antibody diluted in PBS-T-FCS was distributed in an amount of 100 µl per well. The secondary antibodies used were conjugated to peroxidase and directed against the mouse immunoglobulins: Ig(H+L) (4000th, P.A.R.I.S.) or IgA (1000th, Caltag). The plates were then incubated for 2 hours at 37° C. and washed 5 times. The plates were then incubated with the peroxidase substrate (TMB, 100 µl per well) for 10 minutes in darkness. The enzyme reaction was stopped by addition of 50 µl of 2M $H_3PO_4$. The optical densities (OD) were read at 450 nm (Dynex reader). The $OD_{450}$=f(dilution) curve was modelized by the regression curve y=(b+cx)/(1+ax) with the aid of Origin software. The antibody titer was determined as the dilution value giving twice the $OD_{450}$ of a control sample (d0) at its greatest dilution.

I.6 Production of IFN-γ/IL-5/IL-10 by T Lymphocytes Specific for N—PΔN or GFP
The spleen and the ganglions draining the respiratory tract (facial, cervical and mediastinal) were treated according to the same protocol. The spleens were treated individually and the ganglions were grouped by test groups.
The lymphoid organs were sliced thinly and then ground delicately on a filter (100 µm cellular sieve, BD Falcon) in RPMI medium and PS. The cell suspension was centrifuged at 1700 rpm for 10 minutes at 4° C. The cells were resuspended in 1 ml of erythrocyte lysis buffer (hypotonic saline buffer) and incubated for 5 minutes at room temperature. The lysis reaction was stopped by addition of 10 ml of complete RPMI (PS, 2 mM L-glutamine and 10% FCS). The membrane debris were decanted and the cells were washed three times by centrifugation (1700 rpm for 10 minutes at 4° C.). The cell suspensions were counted with the aid of a Malassez cell.
The cells were cultured in cell-culture treated 96-well microplates culture (Falcon) in an amount of 400,000 cells per well in 200 µl of complete RPMI medium. Four culture conditions were tested in triplicate on each cell suspension:
PMA (phorbol 12-myristate 13-acetate, Sigma) 10 ng/ml and ionomycin (Sigma) 1 µg/ml (positive control, polyclonal activation)
complete RPMI (negative control)
N—PΔN 10 µg/ml
GFP 10 µg/ml.
After 48 hours (IL-5 and IL-10) or 72 hours (IFN-γ) culturing at 37° C. with 5% $CO_2$, the culture supernatants were collected and frozen at −20° C. until titration of the cytokines by ELISA:
96-well plates (Immulon 2HB, ThermoLabsystems) were sensitized overnight at 4° C. with mouse anti-cytokine capture antibody at 4 µg/ml (IFN-γ) or 2 µg/ml (IL-5/IL-10) in 0.1 M bicarbonate buffer, pH 9.5 (100 µl/well). The plates were washed 5 times with 200 µl per well of 0.05% PBS-Tween 20 (use of a Wellwash device, Labsystems). The plates were then saturated for 2 hours at 37° C. with 150 µl per well of 0.05% PBS-Tween 20 buffer and 2% bovine serum albumin (PBS-T-BSA). After 5 washes, the recombinant mouse cytokine reference and the samples to be titrated were diluted in PBS-T-BSA by successive dilutions to half. Four successive dilutions to half were carried out on the pure samples. The plate was then incubated overnight at 4° C. After 5 washes, the biotinylated detection antibody was distributed (1 µg/ml for IFN-γ/IL-10 or 0.5 µg/ml for IL-5 in PBS-T-BSA, 100 µl/well) and incubated for 3 hours at 4° C. After 5 washes, the streptavidin-peroxidase conjugate (Pierce) was distributed (1 µg/ml in PBS-T-BSA, 100 µl/well) and incubated for one hour at 4° C. After 5 washes, the peroxidase substrate (ABTS+$H_2O_2$) was distributed in the wells. After incubation for 45 minutes, the optical densities were read at 405 nm (Dynex ELISA reader). The concentration of IFN-γ/IL-5/IL-10 in the samples was calculated relative to the standard range using the analysis software "Revelation" coupled with the reader.

Antibody References (BD Bioscience):

IFN-γ: capture antibody: clone R4-6A2 (BD Bioscience, 551216)

detection antibody: clone XMG1.2 (BD Bioscience, ref 554410)

recombinant mIFN-γ: R&D systems 485-MI

IL-5: capture antibody: clone TRFK5 (BD Bioscience, 554393)

detection antibody: clone TRFK4 (BD Bioscience, ref 554397)

recombinant mIL-5: BD Bioscience 554581

IL-10: capture antibody: clone JES5-2A5 (BD Bioscience, 551215)

detection antibody: clone SXC-1 (BD Bioscience, ref 554423)

recombinant mIL-10: BD Bioscience 550070 streptavidin peroxidase Immunopure (Pierce 21126)

I.7 Statistical Analyses:

The groups were compared in pairs by carrying out a Mann-Whitney U test (http://eatworms.swmed.edu/~leon/stats/utest.html). A value of p<0.05 was considered to be significant.

II. Results:

In order to evaluate the potential of the rings formed by the N—PΔN complex as a vaccinal vector, BALB/c mice were immunized against GFP (model antigen) in the form of a fusion protein with the N nucleoprotein of RSV. The N-GFP fusion protein forms soluble ring structures which can be purified by the method previously described (patent FR0504426). NGFP—PΔN protein complexes are thus obtained. For vaccinal use, the N-GFP and P proteins can be separated, but that operation is not necessary, the inventors' previous results on the immunogenicity of the N rings having shown that the presence of PΔN does not have a negative effect.

Given the works directed at pathogens targeting the respiratory paths and the demonstrated immunogenicity of the N—PΔN complexes when administered by the nasal route, that is the favored administration route for demonstrating the vector properties of those complexes. Groups of mice were also immunized against the GFP protein in its native recombinant form and against the N—PΔN complexes. The detoxified lymphotoxin of *E. Coli*, LT(R192G), whose adjuvant properties by the mucosal route have been well documented (McNeal et al. 2002, Freytag and Clements 2005), was used as adjuvant for all the groups of animals in this example.

The parameters of the immune response directed against GFP and against N—PΔN which were monitored are (i) the production of serum and mucosal antibodies (by bronchoalveolar washing) and (ii) the cell response via the production of cytokines (IFN-γ, IL-5 and IL-10) by memory T lymphocytes isolated from the spleen or the ganglions draining the respiratory tract.

II-1 The Rings of N are an Effective Vector for Targeting Antibodies Against an Exogenous Antigen, Example of GFP The N—PΔN complexes are very highly immunogenic by the systemic route and by the mucosal route (patent FR0504426). The fusion of GFP with the N protein does not alter the intensity of the anti-N—PΔN Ac response, either at serum level (FIG. 3B) or at mucosal level (FIG. 3C): there is no significant difference between the groups N-GFP—PΔN and N—PΔN.

GFP administered by the nasal route induces a systemic Ac response (FIG. 3A; GFP versus control, p=0.003) but not a local response (FIG. 3C; GFP versus control, not significant).

On the other hand, the association of GFP with the N—PΔN complexes greatly increases the rate of anti-GFP antibodies as compared with GFP alone. The level of anti-GFP antibodies is multiplied by a factor of 4 at serum level (N-GFP—PΔN versus GFP, p=0.039) and by a factor of 100 at BAW level (N-GFP—PΔN versus GFP, p=0.014).

II-2 The Vectorization of GFP on the N Rings Does Not Increase the Specific T Response:

In addition to their strong ability to stimulate the antibody response, the N—PΔN effectively stimulate the memory T response demonstrated by a synthesis of antigen-dependent IFN-γ at systemic level (patent FR0504426 and FIG. 4, N—PΔN spleens versus control, p=0.01) but also at local level (FIG. 5, locoregional ganglions). The fusion of an exogenous antigen such as GFP to the N does not interfere with the establishment of those T responses, either at the level of the spleen (N-GFP—PΔN versus N—PΔN, not different) or at the level of the ganglions (FIG. 4).

On the other hand, whatever the mode of presentation of the GFP (alone or fused to N), no T response specific for GFP, measured by the production of IFN-γ (FIG. 4) or of IL-5/IL-10 (not shown), is observed: there is no significant difference between the control groups. N-GFP—PΔN and GFP.

In conclusion, the example of GFP made it possible to demonstrate that the N—PΔN complexes are very powerful antigen vectors for stimulating antibody responses, in particular at mucosal level. On the other hand, they are found to have little effectiveness in stimulating a memory T response against the same antigens. It is important to note that the fusion of an exogenous antigen did not alter the immunogenicity proper to the N—PΔN complexes.

These results make it possible to envisage using N—PΔN complexes as an antigen vector with the aim of stimulating strong antibody responses. Within the scope of vaccination against RSV, the results obtained show that it is possible to take advantage both of the cell response against the nucleoprotein and of an antibody response against antigens/epitopes of RSV which are known to be the target of neutralizing antibodies. These two facets of the immune defenses are critical in obtaining sterilizing immunity against RSV.

In general, for many pathogens (in particular viruses), the target epitopes or antigens of the neutralizing antibodies are well described in the literature and participate in the effective control of the infection. Novel vectors for effectively stimulating those responses are therefore highly desirable for vaccination. The N—PΔN complexes further have the advantage of being inert, non-replicative structures, without any risk for the host or the environment.

Example 6

Optimization of the Linker Sequence Between the N Protein and the GFP Protein Purification of the N-GFP fusion proteins was carried out by affinity with protein P (fragment 161-241) fused to GST. The protein N-GFP constructed according to Example 1 (SEQ ID NO:33) was purified with a yield that is ten times lower than that of protein N. In addition, the presence of two polypeptides that migrate with an apparent mass of approximately 43 kDa was still observed. Those bands were analyzed by mass spectrometry (MALDI-TOF). They correspond to a cleavage which took place (i) in the linker sequence separating N from GFP (at the level of an arginine), resulting in the addition of 11 residues at the C-terminal end of the N protein, and (ii) in the C-terminal part of the N protein (at the level of a lysine) by removing the last 6 residues. The construction of a N protein deleted of 6, 12 and 27 residues at the C-terminal end has shown that the proteins NΔ6C and NΔ12C still interact with P, unlike the truncated form NΔ27C.

The linker sequence between N and GFP was therefore modified, the sequence KLRILQSTVPRIARDPPVAT (SEQ ID NO: 34, the arrow indicates the cleavage site in *E. Coli*) being replaced by the sequence KLRILQSTVPSERPQAS-GVYMGNLT

```
             305                 310                 315                 320
Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
                340                 345                 350

Tyr Ala Glu Gln Leu Lys Glu Asn Gly Val Ile Asn Tyr Ser Val Leu
                355                 360                 365

Asp Leu Thr Ala Glu Glu Leu Glu Ala Ile Lys His Gln Leu Asn Pro
            370                 375                 380

Lys Asp Asn Asp Val Glu Leu
385                 390

<210> SEQ ID NO 2
<211> LENGTH: 391
<212> TYPE: PRT
<213> ORGANISM: Bovine respiratory syncytial virus

<400> SEQUENCE: 2

Met Ala Leu Ser Lys Val Lys Leu Asn Asp Thr Phe Asn Lys Asp Gln
1               5                   10                  15

Leu Leu Ser Thr Ser Lys Tyr Thr Ile Gln Arg Ser Thr Gly Asp Asn
                20                  25                  30

Ile Asp Ile Pro Asn Tyr Asp Val Gln Lys His Leu Asn Lys Leu Cys
            35                  40                  45

Gly Met Leu Leu Ile Thr Glu Asp Ala Asn His Lys Phe Thr Gly Leu
        50                  55                  60

Ile Gly Met Leu Tyr Ala Met Ser Arg Leu Gly Arg Glu Asp Thr Leu
65                  70                  75                  80

Lys Ile Leu Lys Asp Ala Gly Tyr Gln Val Arg Ala Asn Gly Val Asp
                85                  90                  95

Val Ile Thr His Arg Gln Asp Val Asn Gly Lys Glu Met Lys Phe Glu
            100                 105                 110

Val Leu Thr Leu Val Ser Leu Thr Ser Glu Val Gln Gly Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Phe Pro Asp Cys Gly Met Ile Val
145                 150                 155                 160

Leu Cys Val Ala Ala Leu Val Ile Thr Lys Leu Ala Ala Gly Asp Arg
                165                 170                 175

Ser Gly Leu Thr Ala Val Ile Arg Arg Ala Asn Asn Val Leu Arg Asn
            180                 185                 190

Glu Met Lys Arg Tyr Lys Gly Leu Ile Pro Lys Asp Ile Ala Asn Ser
        195                 200                 205

Phe Tyr Glu Val Phe Glu Lys Tyr Pro His Tyr Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285

Glu Tyr Ala Gln Lys Leu Gly Gly Glu Ala Gly Phe Tyr His Ile Leu
```

```
                    290                 295                 300
Asn Asn Pro Lys Ala Ser Leu Leu Ser Leu Thr Gln Phe Pro Asn Phe
305                 310                 315                 320

Ser Ser Val Val Leu Gly Asn Ala Ala Gly Leu Gly Ile Met Gly Glu
                    325                 330                 335

Tyr Arg Gly Thr Pro Arg Asn Gln Asp Leu Tyr Asp Ala Ala Lys Ala
                    340                 345                 350

Tyr Ala Glu Gln Leu Lys Glu Asn Gly Val Ile Asn Tyr Ser Val Leu
                    355                 360                 365

Asp Leu Thr Thr Glu Glu Leu Glu Ala Ile Lys Asn Gln Leu Asn Pro
                    370                 375                 380

Lys Asp Asn Asp Val Glu Leu
385                 390

<210> SEQ ID NO 3
<211> LENGTH: 524
<212> TYPE: PRT
<213> ORGANISM: Sendai virus

<400> SEQUENCE: 3

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
                20                  25                  30

Ser Thr Val Ser Val Phe Val Leu Gly Pro Ser Val Thr Asp Asp Ala
                35                  40                  45

Asp Lys Leu Phe Ile Ala Thr Thr Phe Leu Ala His Ser Leu Asp Thr
                50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
                100                 105                 110

Thr Lys Thr Asp Gly Phe Ile Val Lys Thr Arg Asp Met Glu Tyr Glu
                115                 120                 125

Arg Thr Thr Glu Trp Leu Phe Gly Pro Met Val Asn Lys Ser Pro Leu
                130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
                180                 185                 190

Phe Asn Arg Leu Glu Ala Phe Arg Gln Asp Gly Thr Val Lys Gly Ala
                195                 200                 205

Leu Val Phe Thr Gly Glu Thr Val Glu Gly Ile Gly Ser Val Met Arg
                210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
                260                 265                 270

Ile Lys Tyr Gly Val Glu Thr Lys Met Ala Ala Leu Thr Leu Ser Asn
```

```
                    275                 280                 285
Leu Arg Pro Asp Ile Asn Lys Leu Arg Ser Leu Ile Asp Thr Tyr Leu
290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Gln Asn Lys Ala Met Gln Gln Tyr Val Thr
                340                 345                 350

Gly Arg Thr Tyr Leu Asp Met Glu Met Phe Leu Leu Gly Gln Ala Val
                355                 360                 365

Ala Lys Asp Ala Glu Ser Lys Ile Ser Ser Ala Leu Glu Asp Glu Leu
        370                 375                 380

Gly Val Thr Asp Thr Ala Lys Glu Arg Leu Arg His His Leu Ala Asn
385                 390                 395                 400

Leu Ser Gly Gly Asp Gly Ala Tyr His Lys Pro Thr Gly Gly Gly Ala
                405                 410                 415

Ile Glu Val Ala Leu Asp Asn Ala Asp Ile Asp Leu Glu Pro Glu Ala
                420                 425                 430

His Thr Asp Gln Asp Ala Arg Gly Trp Gly Gly Asp Ser Gly Asp Arg
        435                 440                 445

Trp Ala Arg Ser Thr Ser Ser Gly His Phe Ile Thr Leu His Gly Ala
        450                 455                 460

Glu Arg Leu Glu Glu Thr Asn Asp Glu Asp Val Ser Asp Ile Glu
465                 470                 475                 480

Arg Arg Ile Ala Arg Arg Leu Ala Glu Arg Gln Glu Asp Ala Thr
                485                 490                 495

Thr His Glu Asp Glu Gly Arg Asn Asn Gly Val Asp His Asp Glu Glu
                500                 505                 510

Asp Asp Ala Ala Ala Ala Gly Met Gly Gly Ile
        515                 520

<210> SEQ ID NO 4
<211> LENGTH: 525
<212> TYPE: PRT
<213> ORGANISM: Measles virus

<400> SEQUENCE: 4

Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ile Ser Ser Asp Gln Ser Arg Phe
```

```
            130                 135                 140
Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
        195                 200                 205

Phe Arg Leu Glu Arg Lys Trp Leu Asp Val Val Arg Asn Arg Ile Ala
210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
370                 375                 380

Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
                405                 410                 415

Val Ser Phe Leu His Gly Asp Gln Ser Glu Asn Glu Leu Pro Arg Leu
            420                 425                 430

Gly Gly Lys Glu Asp Arg Arg Val Lys Gln Ser Arg Gly Glu Ala Arg
        435                 440                 445

Glu Ser Tyr Arg Glu Thr Gly Pro Ser Arg Ala Ser Asp Ala Arg Ala
450                 455                 460

Ala His Leu Pro Thr Gly Thr Pro Leu Asp Ile Asp Thr Ala Ser Glu
465                 470                 475                 480

Ser Ser Gln Asp Pro Gln Asp Ser Arg Arg Ser Ala Asp Ala Leu Leu
                485                 490                 495

Arg Leu Gln Ala Met Ala Gly Ile Ser Glu Glu Gln Gly Ser Asp Thr
            500                 505                 510

Asp Thr Pro Ile Val Tyr Asn Asp Arg Asn Leu Leu Asp
        515                 520                 525

<210> SEQ ID NO 5
<211> LENGTH: 553
<212> TYPE: PRT
<213> ORGANISM: Mumps virus
```

<400> SEQUENCE: 5

```
Met Ser Ser Val Leu Lys Ala Phe Glu Arg Phe Thr Ile Glu Gln Glu
1               5                   10                  15

Leu Gln Asp Arg Gly Glu Gly Ser Ile Pro Pro Glu Thr Leu Lys
            20                  25                  30

Ser Ala Val Lys Val Phe Val Ile Asn Thr Pro Asn Pro Thr Thr Arg
            35                  40                  45

Tyr Gln Met Leu Asn Phe Cys Leu Arg Ile Ile Cys Ser Gln Asn Arg
50                  55                  60

Arg Ala Ser His Arg Val Gly Ala Leu Ile Ala Leu Phe Ser Leu Pro
65                  70                  75                  80

Ser Ala Gly Met Gln Asn His Ile Arg Leu Ala Asp Arg Ser Pro Glu
                85                  90                  95

Ala Gln Ile Glu Arg Cys Glu Ile Asp Gly Phe Glu Pro Gly Thr Tyr
            100                 105                 110

Arg Leu Ile Pro Asn Ala Arg Ala Asn Leu Thr Ala Asn Glu Ile Ala
            115                 120                 125

Ala Tyr Ala Leu Leu Ala Asp Asp Leu Pro Pro Thr Ile Asn Asn Gly
130                 135                 140

Thr Pro Tyr Val His Ala Asp Val Glu Leu Gln Pro Cys Asp Glu Ile
145                 150                 155                 160

Glu Gln Phe Leu Asp Arg Cys Tyr Ser Val Leu Ile Gln Ala Trp Val
                165                 170                 175

Met Val Cys Lys Cys Met Thr Ala Tyr Asp Gln Pro Ala Gly Ser Ala
            180                 185                 190

Asp Arg Arg Phe Ala Lys Tyr Gln Gln Gln Gly Arg Leu Glu Ala Arg
            195                 200                 205

Tyr Met Leu Gln Pro Glu Ala Gln Arg Leu Ile Gln Thr Ala Ile Arg
210                 215                 220

Lys Ser Leu Val Val Arg Gln Tyr Leu Thr Phe Glu Leu Gln Leu Ala
225                 230                 235                 240

Arg Arg Gln Gly Leu Leu Ser Asn Arg Tyr Tyr Ala Met Val Gly Asp
                245                 250                 255

Ile Gly Lys Tyr Ile Glu Asn Ser Gly Leu Thr Ala Phe Phe Leu Thr
            260                 265                 270

Leu Lys Tyr Ala Leu Gly Thr Lys Trp Ser Pro Leu Ser Leu Ala Ala
            275                 280                 285

Phe Thr Gly Glu Leu Thr Lys Leu Arg Ser Leu Met Met Leu Tyr Arg
290                 295                 300

Asp Ile Gly Glu Gln Ala Arg Tyr Leu Ala Leu Leu Glu Ala Pro Gln
305                 310                 315                 320

Ile Met Asp Phe Ala Pro Gly Gly Tyr Pro Leu Ile Phe Ser Tyr Ala
                325                 330                 335

Met Gly Val Gly Ser Val Leu Asp Val Gln Met Arg Asn Tyr Thr Tyr
            340                 345                 350

Ala Arg Pro Phe Leu Asn Gly Tyr Tyr Phe Gln Ile Gly Val Glu Thr
            355                 360                 365

Ala Arg Arg Gln Gln Gly Thr Val Asp Asn Arg Val Ala Asp Asp Leu
370                 375                 380

Gly Leu Thr Pro Glu Gln Arg Asn Glu Val Thr Gln Leu Val Asp Arg
385                 390                 395                 400

Leu Ala Arg Gly Arg Gly Ala Gly Ile Pro Gly Gly Pro Val Asn Pro
                405                 410                 415
```

```
Phe Val Pro Pro Val Gln Gln Gln Pro Ala Ala Val Tyr Ala Asp
            420                 425                 430

Ile Pro Ala Leu Glu Glu Ser Asp Asp Gly Asp Glu Asp Gly Gly
            435                 440                 445

Ala Gly Phe Gln Asn Gly Val Gln Val Pro Ala Val Arg Gln Gly Gly
            450                 455                 460

Gln Thr Asp Phe Arg Ala Gln Pro Leu Gln Asp Pro Ile Gln Ala Gln
465                 470                 475                 480

Leu Phe Met Pro Leu Tyr Pro Gln Val Ser Asn Ile Pro Asn Asn Arg
                485                 490                 495

Ile Ile Arg Ser Ile Ala Ser Gly Gly Trp Lys Thr Lys Ile Tyr Tyr
                500                 505                 510

Asp Thr Thr Arg Met Val Ile Leu Asn Lys Met Gln Gly Ala Asn Thr
                515                 520                 525

Glu Thr Leu Ser Gln Thr Ile Pro Ile Lys Thr His Ser Cys Lys Trp
530                 535                 540

Ala Thr Gly Met Ser Lys Ser Leu Thr
545                 550

<210> SEQ ID NO 6
<211> LENGTH: 394
<212> TYPE: PRT
<213> ORGANISM: Human Metapneumovirus

<400> SEQUENCE: 6

Met Ser Leu Gln Gly Ile His Leu Ser Asp Leu Ser Tyr Lys His Ala
1               5                   10                  15

Ile Leu Lys Glu Ser Gln Tyr Thr Ile Lys Arg Asp Val Gly Thr Thr
                20                  25                  30

Thr Ala Val Thr Pro Ser Ser Leu Gln Gln Glu Ile Thr Leu Leu Cys
            35                  40                  45

Gly Glu Ile Leu Tyr Ala Lys His Ala Asp Tyr Lys Tyr Ala Ala Glu
        50                  55                  60

Ile Gly Ile Gln Tyr Ile Ser Thr Ala Leu Gly Ser Glu Arg Val Gln
65                  70                  75                  80

Gln Ile Leu Arg Asn Ser Gly Ser Glu Val Gln Val Val Leu Thr Arg
                85                  90                  95

Thr Tyr Ser Leu Gly Lys Ile Lys Asn Asn Lys Gly Glu Asp Leu Gln
            100                 105                 110

Met Leu Asp Ile His Gly Val Glu Lys Ser Trp Val Glu Glu Ile Asp
        115                 120                 125

Lys Glu Ala Arg Lys Thr Met Ala Thr Leu Leu Lys Glu Ser Ser Gly
130                 135                 140

Asn Ile Pro Gln Asn Gln Arg Pro Ser Ala Pro Asp Thr Pro Ile Ile
145                 150                 155                 160

Leu Leu Cys Val Gly Ala Leu Ile Phe Thr Lys Leu Ala Ser Thr Ile
                165                 170                 175

Glu Val Gly Leu Glu Thr Thr Val Arg Arg Ala Asn Arg Val Leu Ser
            180                 185                 190

Asp Ala Leu Lys Arg Tyr Pro Arg Met Asp Ile Pro Lys Ile Ala Arg
        195                 200                 205

Ser Phe Tyr Asp Leu Phe Glu Gln Lys Val Tyr His Arg Ser Leu Phe
210                 215                 220

Ile Glu Tyr Gly Lys Ala Leu Gly Ser Ser Ser Thr Gly Ser Lys Ala
225                 230                 235                 240
```

```
Glu Ser Leu Phe Val Asn Ile Phe Met Gln Ala Tyr Gly Ala Gly Gln
                245                 250                 255

Thr Met Leu Arg Trp Gly Val Ile Ala Arg Ser Ser Asn Asn Ile Met
            260                 265                 270

Leu Gly His Val Ser Val Gln Ala Glu Leu Lys Gln Val Thr Glu Val
        275                 280                 285

Tyr Asp Leu Val Arg Glu Met Gly Pro Glu Ser Gly Leu Leu His Leu
    290                 295                 300

Arg Gln Ser Pro Lys Ala Gly Leu Leu Ser Leu Ala Asn Cys Pro Asn
305                 310                 315                 320

Phe Ala Ser Val Val Leu Gly Asn Ala Ser Gly Leu Gly Ile Ile Gly
                325                 330                 335

Met Tyr Arg Gly Arg Val Pro Asn Thr Glu Leu Phe Ser Ala Ala Glu
            340                 345                 350

Ser Tyr Ala Lys Ser Leu Lys Glu Ser Asn Lys Ile Asn Phe Ser Ser
        355                 360                 365

Leu Gly Leu Thr Asp Glu Glu Lys Glu Ala Ala Glu His Phe Leu Asn
    370                 375                 380

Val Ser Asp Asp Ser Gln Asn Asp Tyr Glu
385                 390

<210> SEQ ID NO 7
<211> LENGTH: 241
<212> TYPE: PRT
<213> ORGANISM: Human respiratory syncytial virus

<400> SEQUENCE: 7

Met Glu Lys Phe Ala Pro Glu Phe His Gly Glu Asp Ala Asn Asn Arg
1               5                   10                  15

Ala Thr Lys Phe Leu Glu Ser Ile Lys Gly Lys Phe Thr Ser Pro Lys
            20                  25                  30

Asp Pro Lys Lys Lys Asp Ser Ile Ile Ser Val Asn Ser Thr Asp Ile
        35                  40                  45

Glu Val Thr Lys Glu Ser Pro Ile Thr Ser Asn Ser Thr Ile Ile Asn
    50                  55                  60

Pro Thr Asn Glu Thr Asp Asp Asn Ala Gly Asn Lys Pro Asn Tyr Gln
65                  70                  75                  80

Arg Lys Pro Leu Val Ser Phe Lys Glu Asp Pro Ile Pro Ser Asp Asn
                85                  90                  95

Pro Phe Ser Lys Leu Tyr Lys Glu Thr Ile Glu Thr Phe Asp Asn Asn
            100                 105                 110

Glu Glu Glu Ser Ser Tyr Ser Tyr Glu Glu Ile Asn Asp Gln Thr Asn
        115                 120                 125

Asp Asn Ile Thr Ala Arg Leu Asp Arg Ile Asp Glu Lys Leu Ser Glu
130                 135                 140

Ile Leu Gly Met Leu His Thr Leu Val Val Ala Ser Ala Gly Pro Thr
145                 150                 155                 160

Ser Ala Arg Asp Gly Ile Arg Asp Ala Met Val Gly Leu Arg Glu Glu
                165                 170                 175

Met Ile Glu Lys Ile Arg Thr Glu Ala Leu Met Thr Asn Asp Arg Leu
            180                 185                 190

Glu Ala Met Ala Arg Leu Arg Asn Glu Glu Ser Glu Lys Met Ala Lys
        195                 200                 205

Asp Thr Ser Asp Glu Val Ser Leu Asn Pro Thr Ser Glu Lys Leu Asn
    210                 215                 220
```

```
Asn Leu Leu Glu Gly Asn Asp Ser Asp Asn Asp Leu Ser Leu Glu Asp
225                 230                 235                 240

Phe

<210> SEQ ID NO 8
<211> LENGTH: 241
<212> TYPE: PRT
<213> ORGANISM: Bovine respiratory syncytial virus

<400> SEQUENCE: 8

Met Glu Lys Phe Ala Pro Glu Phe His Gly Glu Asp Ala Asn Thr Lys
1               5                   10                  15

Ala Thr Lys Phe Leu Glu Ser Leu Lys Gly Lys Phe Thr Ser Ser Lys
                20                  25                  30

Asp Ser Arg Lys Lys Asp Ser Ile Ile Ser Val Asn Ser Ile Asp Ile
            35                  40                  45

Glu Leu Pro Lys Glu Ser Pro Ile Thr Ser Thr Asn His Asn Ile Asn
50                  55                  60

Gln Pro Ser Glu Ile Asn Asp Thr Ile Ala Ala Asn Gln Val His Ile
65                  70                  75                  80

Arg Lys Pro Leu Val Ser Phe Lys Glu Glu Leu Pro Ser Ser Glu Asn
                85                  90                  95

Pro Phe Thr Lys Leu Tyr Lys Glu Thr Ile Glu Thr Phe Asp Asn Asn
            100                 105                 110

Glu Glu Glu Ser Ser Tyr Ser Tyr Asp Glu Ile Asn Asp Gln Thr Asn
        115                 120                 125

Asp Asn Ile Thr Ala Arg Leu Asp Arg Ile Asp Glu Lys Leu Ser Glu
    130                 135                 140

Ile Ile Gly Met Leu His Thr Leu Val Val Ala Ser Ala Gly Pro Thr
145                 150                 155                 160

Ala Ala Arg Asp Gly Ile Arg Asp Ala Met Val Gly Leu Arg Glu Glu
                165                 170                 175

Met Ile Glu Lys Ile Arg Ser Glu Ala Leu Met Thr Asn Asp Arg Leu
            180                 185                 190

Glu Ala Met Ala Arg Leu Arg Asp Glu Ser Glu Lys Met Thr Lys
        195                 200                 205

Asp Thr Ser Asp Glu Val Lys Leu Thr Pro Thr Ser Glu Lys Leu Asn
    210                 215                 220

Met Val Leu Glu Asp Glu Ser Ser Asp Asn Asp Leu Ser Leu Glu Asp
225                 230                 235                 240

Phe

<210> SEQ ID NO 9
<211> LENGTH: 568
<212> TYPE: PRT
<213> ORGANISM: Sendai virus

<400> SEQUENCE: 9

Met Asp Gln Asp Ala Phe Ile Leu Lys Glu Asp Ser Glu Val Glu Arg
1               5                   10                  15

Glu Ala Pro Gly Gly Arg Glu Ser Leu Ser Asp Val Ile Gly Phe Leu
                20                  25                  30

Asp Ala Val Leu Ser Ser Glu Pro Thr Asp Ile Gly Gly Asp Arg Ser
            35                  40                  45

Trp Leu His Asn Thr Ile Asn Thr Pro Gln Gly Pro Gly Ser Ala His
50                  55                  60
```

```
Arg Ala Lys Ser Glu Gly Glu Gly Val Ser Thr Pro Ser Thr Gln
 65                  70                  75                  80

Asp Asn Arg Ser Gly Glu Glu Ser Arg Val Ser Gly Arg Thr Ser Lys
                 85                  90                  95

Pro Glu Ala Glu Ala His Ala Gly Asn Leu Asp Lys Gln Asn Ile His
            100                 105                 110

Arg Ala Phe Gly Gly Arg Thr Gly Thr Asn Ser Val Ser Gln Asp Leu
            115                 120                 125

Gly Asp Gly Gly Asp Ser Gly Ile Leu Glu Asn Pro Pro Asn Glu Arg
        130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
            180                 185                 190

Asn Asn Gly Arg Ser Met Glu Pro Gly Ser Ser His Ser Ala Arg Val
            195                 200                 205

Thr Gly Val Leu Val Ile Pro Ser Pro Glu Leu Glu Glu Ala Val Leu
210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
            275                 280                 285

Pro Ile Gly Thr Arg Ser Val Ser Asp Cys Pro Ala Asn Gly Arg Pro
        290                 295                 300

Ile His Pro Gly Leu Glu Ser Asp Ser Thr Lys Lys Gly Ile Gly Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Arg Arg Ala Leu Lys Ser Ala Asn Tyr Ala Glu Met Thr
            355                 360                 365

Phe Asn Val Cys Gly Leu Ile Leu Ser Ala Glu Lys Ser Ser Ala Arg
        370                 375                 380

Lys Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Thr Asp Ser Leu Thr Arg Ser Pro
            435                 440                 445

Ser Val Phe Ala Lys Ser Lys Glu Asn Lys Thr Lys Ala Thr Arg Phe
        450                 455                 460

Asp Pro Ser Met Glu Thr Leu Glu Asp Met Lys Tyr Lys Pro Asp Leu
465                 470                 475                 480

Ile Arg Glu Asp Glu Phe Arg Asp Glu Ile Arg Asn Pro Val Tyr Gln
                485                 490                 495
```

```
Glu Arg Asp Thr Glu Pro Arg Ala Ser Asn Ala Ser Arg Leu Leu Pro
            500                 505                 510

Ser Lys Glu Lys Pro Thr Met His Ser Leu Arg Leu Val Ile Glu Ser
            515                 520                 525

Ser Pro Leu Ser Arg Ala Glu Lys Ala Ala Tyr Val Lys Ser Leu Ser
        530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565

<210> SEQ ID NO 10
<211> LENGTH: 507
<212> TYPE: PRT
<213> ORGANISM: Measles virus

<400> SEQUENCE: 10

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Val Glu Glu Ala
            20                  25                  30

Met Ala Ala Trp Ser Glu Ile Ser Asp Asn Pro Gly Gln Asp Arg Ala
        35                  40                  45

Thr Cys Lys Glu Glu Glu Ala Gly Ser Ser Gly Leu Ser Lys Pro Cys
    50                  55                  60

Leu Ser Ala Ile Gly Ser Thr Glu Gly Gly Ala Pro Arg Ile Arg Gly
65                  70                  75                  80

Gln Gly Ser Gly Glu Ser Asp Asp Asp Ala Glu Thr Leu Gly Ile Pro
                85                  90                  95

Ser Arg Asn Leu Gln Ala Ser Ser Thr Gly Leu Gln Cys Tyr His Val
            100                 105                 110

Tyr Asp His Ser Gly Glu Ala Val Lys Gly Ile Gln Asp Ala Asp Ser
        115                 120                 125

Ile Met Val Gln Ser Gly Leu Asp Gly Asp Ser Thr Leu Ser Gly Gly
    130                 135                 140

Asp Asp Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Lys Leu Gln Ser Arg Gly Asn Asn Phe Pro Lys Leu Gly Lys
        195                 200                 205

Thr Leu Asn Val Pro Pro Pro Pro Asn Pro Ser Arg Ala Ser Thr Ser
    210                 215                 220

Glu Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
        275                 280                 285

Ser Gly Thr Thr Ile Ser Pro Arg Ser Gln Asn Asn Glu Glu Gly Gly
    290                 295                 300
```

```
Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
            325                 330                 335

Glu Ser Leu Leu Leu Lys Gly Val Glu Ser Ile Lys Lys Gln
        340                 345                 350

Ile Asn Arg Gln Asn Ile Ser Ile Ser Thr Leu Glu Gly His Leu Ser
            355                 360                 365

Ser Ile Met Ile Ala Ile Pro Gly Leu Gly Lys Asp Pro Asn Asp Pro
370                 375                 380

Thr Ala Asp Val Glu Leu Asn Pro Asp Leu Lys Pro Ile Ile Gly Arg
385                 390                 395                 400

Asp Ser Gly Arg Ala Leu Ala Glu Val Leu Lys Lys Pro Val Ala Ser
                405                 410                 415

Arg Gln Leu Gln Gly Met Thr Asn Gly Arg Thr Ser Ser Arg Gly Gln
            420                 425                 430

Leu Leu Lys Glu Phe Gln Leu Lys Pro Ile Gly Lys Lys Val Ser Ser
        435                 440                 445

Ala Val Gly Phe Val Pro Asp Thr Gly Pro Ala Ser Arg Ser Val Ile
    450                 455                 460

Arg Ser Ile Ile Lys Ser Ser Arg Leu Glu Glu Asp Arg Lys Arg Tyr
465                 470                 475                 480

Leu Met Thr Leu Leu Asp Asp Ile Lys Gly Ala Asn Asp Leu Ala Lys
                485                 490                 495

Phe His Gln Met Leu Met Lys Ile Ile Met Lys
                500                 505

<210> SEQ ID NO 11
<211> LENGTH: 390
<212> TYPE: PRT
<213> ORGANISM: Mumps virus

<400> SEQUENCE: 11

Met Asp Gln Phe Ile Lys Gln Asp Glu Thr Gly Asp Leu Ile Glu Thr
1               5                   10                  15

Gly Met Asn Val Ala Asn His Phe Leu Ser Ala Pro Ile Gln Gly Thr
            20                  25                  30

Asn Ser Leu Ser Lys Ala Ser Ile Ile Pro Gly Val Ala Pro Val Leu
        35                  40                  45

Ile Gly Asn Pro Glu Gln Lys Asn Ile Gln His Pro Thr Ala Ser His
    50                  55                  60

Gln Gly Ser Lys Ser Lys Gly Ser Gly Ser Val Arg Ser Ile Ile
65                  70                  75                  80

Val Pro Pro Ser Glu Ala Ser Asn Gly Gly Thr Gln Ile Pro Glu Pro
                85                  90                  95

Leu Phe Ala Gln Thr Gly Gln Gly Gly Ile Val Thr Thr Val Tyr Gln
            100                 105                 110

Asp Pro Thr Ile Gln Pro Thr Gly Ser Tyr Arg Ser Val Glu Leu Ala
        115                 120                 125

Lys Ile Gly Lys Glu Arg Met Ile Asn Arg Phe Val Glu Lys Pro Arg
    130                 135                 140

Thr Ser Thr Pro Val Thr Glu Phe Lys Arg Gly Ala Gly Ser Arg Ala
145                 150                 155                 160

Gln Gly Gln Thr Ile Gln Glu Glu Gly Ile Asp Gly Asn Gly Ala Ser
                165                 170                 175
```

```
Ala Gly Ser Lys Glu Arg Ser Gly Ser Leu Ser Gly Ala Thr Leu Tyr
            180                 185                 190

Ala His Leu Ser Leu Pro Gln Gln Asp Ser Thr Pro Ala Asn Val Gly
            195                 200                 205

Ile Ala Pro Gln Ser Ala Ile Ser Ala Asn Glu Ile Met Asp Leu Leu
210                 215                 220

Arg Gly Met Asp Ala Arg Leu Gln His Leu Glu Gln Lys Val Asp Lys
225                 230                 235                 240

Val Leu Ala Gln Gly Ser Met Val Thr Gln Ile Lys Asn Glu Leu Ser
                245                 250                 255

Thr Val Lys Thr Thr Leu Ala Thr Ile Glu Gly Met Met Ala Thr Val
                260                 265                 270

Lys Ile Met Asp Pro Gly Asn Pro Thr Gly Val Pro Val Asp Glu Leu
            275                 280                 285

Arg Arg Ser Phe Ser Asp His Val Thr Ile Val Ser Gly Pro Gly Asp
            290                 295                 300

Val Pro Phe Ser Ser Ser Glu Glu Pro Thr Leu Tyr Leu Asp Glu Leu
305                 310                 315                 320

Ala Arg Pro Val Ser Lys Pro Arg Pro Ala Lys Gln Thr Lys Pro Gln
                325                 330                 335

Pro Val Lys Asp Leu Ala Gly Arg Lys Val Met Ile Thr Lys Met Ile
                340                 345                 350

Thr Asp Cys Val Ala Asn Pro Gln Met Lys Gln Ala Phe Glu Gln Arg
            355                 360                 365

Leu Ala Lys Ala Ser Thr Glu Asp Ala Leu Asn Asp Ile Lys Lys Asp
            370                 375                 380

Ile Ile Arg Ser Ala Ile
385                 390

<210> SEQ ID NO 12
<211> LENGTH: 294
<212> TYPE: PRT
<213> ORGANISM: Human Metapneumovirus

<400> SEQUENCE: 12

Met Ser Phe Pro Glu Gly Lys Asp Ile Leu Phe Met Gly Asn Glu Ala
1               5                   10                  15

Ala Lys Leu Ala Glu Ala Phe Gln Lys Ser Leu Arg Lys Pro Gly His
            20                  25                  30

Lys Arg Ser Gln Ser Ile Ile Gly Glu Lys Val Asn Thr Val Ser Glu
        35                  40                  45

Thr Leu Glu Leu Pro Thr Ile Ser Arg Pro Ala Lys Pro Thr Ile Pro
50                  55                  60

Ser Glu Pro Lys Leu Ala Trp Thr Asp Lys Gly Gly Ala Thr Lys Thr
65                  70                  75                  80

Glu Ile Lys Gln Ala Ile Lys Val Met Asp Pro Ile Glu Glu Glu Glu
                85                  90                  95

Ser Thr Glu Lys Lys Val Leu Pro Ser Ser Asp Gly Lys Thr Pro Ala
            100                 105                 110

Glu Lys Lys Leu Lys Pro Ser Thr Asn Thr Lys Lys Val Ser Phe
            115                 120                 125

Thr Pro Asn Glu Pro Gly Lys Tyr Thr Lys Leu Glu Lys Asp Ala Leu
            130                 135                 140

Asp Leu Leu Ser Asp Asn Glu Glu Glu Asp Ala Glu Ser Ser Ile Leu
145                 150                 155                 160
```

```
Thr Phe Glu Glu Arg Asp Thr Ser Ser Leu Ser Ile Glu Ala Arg Leu
                165                 170                 175

Glu Ser Ile Glu Glu Lys Leu Ser Met Ile Leu Gly Leu Leu Arg Thr
            180                 185                 190

Leu Asn Ile Ala Thr Ala Gly Pro Thr Ala Ala Arg Asp Gly Ile Arg
        195                 200                 205

Asp Ala Met Ile Gly Val Arg Glu Gly Leu Ile Ala Asp Ile Ile Lys
    210                 215                 220

Glu Ala Lys Gly Lys Ala Ala Glu Met Met Glu Glu Met Ser Gln
225                 230                 235                 240

Arg Ser Lys Ile Gly Asn Gly Ser Val Lys Leu Thr Glu Lys Ala Lys
                245                 250                 255

Glu Leu Asn Lys Ile Val Glu Asp Glu Ser Thr Ser Gly Glu Ser Glu
            260                 265                 270

Glu Glu Glu Glu Pro Lys Asp Thr Gln Asp Asn Ser Gln Glu Asp Asp
        275                 280                 285

Ile Tyr Gln Leu Ile Met
        290

<210> SEQ ID NO 13
<211> LENGTH: 31
<212> TYPE: DNA
<213> ORGANISM: Artificial
<220> FEATURE:
<223> OTHER INFORMATION: primer

<400> SEQUENCE: 13
gagggatcca tcatggaaaa gtttgctcct g                              31

<210> SEQ ID NO 14
<211> LENGTH: 27
<212> TYPE: DNA
<213> ORGANISM: Artificial
<220> FEATURE:
<223> OTHER INFORMATION: primer

<400> SEQUENCE: 14
ctgttggtgt tgtgtgttga agtgcag                                   27

<210> SEQ ID NO 15
<211> LENGTH: 31
<212> TYPE: DNA
<213> ORGANISM: Artificial
<220> FEATURE:
<223> OTHER INFORMATION: primer

<400> SEQUENCE: 15
gagggatcct ctgctaggga tggtataaga g                              31

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
gagggatcca aaatcagaac tgaagcatta atgacc                         36

<210> SEQ ID NO 17
<211> LENGTH: 34
<212> TYPE: DNA
```

```
<213> ORGANISM: Artificial
<220> FEATURE:
<223> OTHER INFORMATION: primer

<400> SEQUENCE: 17
gagggatccg aggaaagtga aaagatggca aaag                        34

<210> SEQ ID NO 18
<211> LENGTH: 31
<212> TYPE: DNA
<213> ORGANISM: Artificial
<220> FEATURE:
<223> OTHER INFORMATION: primer

<400> SEQUENCE: 18
gagggatccg agaaattgaa caacctgttg g                           31

<210> SEQ ID NO 19
<211> LENGTH: 44
<212> TYPE: DNA
<213> ORGANISM: Artificial
<220> FEATURE:
<223> OTHER INFORMATION: primer

<400> SEQUENCE: 19
gatccaatga tagtgacaat gatctatcac ttgaagattt ctga             44

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20
tcagaaatct tcaagtgata gatcattgtc actatcattg                  40

<210> SEQ ID NO 21
<211> LENGTH: 33
<212> TYPE: DNA
<213> ORGANISM: Artificial
<220> FEATURE:
<223> OTHER INFORMATION: primer

<400> SEQUENCE: 21
gagggatcca tggctcttag caaagtcaag ttg                         33

<210> SEQ ID NO 22
<211> LENGTH: 32
<212> TYPE: DNA
<213> ORGANISM: Artificial
<220> FEATURE:
<223> OTHER INFORMATION: primer

<400> SEQUENCE: 22
ttaactcaaa gctctacatc attatctttt gg                          32

<210> SEQ ID NO 23
<211> LENGTH: 43
<212> TYPE: DNA
<213> ORGANISM: Artificial
<220> FEATURE:
<223> OTHER INFORMATION: primer

<400> SEQUENCE: 23
ccaaaagata atgatgtaga gctctgactc gagcaccacc acc              43
```

```
<210> SEQ ID NO 24
<211> LENGTH: 43
<212> TYPE: DNA
<213> ORGANISM: Artificial
<220> FEATURE:
<223> OTHER INFORMATION: primer

<400> SEQUENCE: 24
ggtggtggtg ctcgagtcag agctctacat cattatcttt tgg                43

<210> SEQ ID NO 25
<211> LENGTH: 55
<212> TYPE: DNA
<213> ORGANISM: Artificial
<220> FEATURE:
<223> OTHER INFORMATION: epitope

<400> SEQUENCE: 25
catggactac aaggacgacg atgacaagca ctggtctatc tctaaaccgc agtag      55

<210> SEQ ID NO 26
<211> LENGTH: 63
<212> TYPE: DNA
<213> ORGANISM: Artificial
<220> FEATURE:
<223> OTHER INFORMATION: epitope

<400> SEQUENCE: 26
tcgactactg cggtttagag atagaccagt gcttgtcatc gtcgtccttg tagtccatga   60
gct                                                                63

<210> SEQ ID NO 27
<211> LENGTH: 40
<212> TYPE: DNA
<213> ORGANISM: Artificial
<220> FEATURE:
<223> OTHER INFORMATION: epitope

<400> SEQUENCE: 27
ccggtctcta ctaacaaagc tgttgtttct ctgagctagt                 40

<210> SEQ ID NO 28
<211> LENGTH: 10
<212> TYPE: PRT
<213> ORGANISM: Artificial
<220> FEATURE:
<223> OTHER INFORMATION: epitope

<400> SEQUENCE: 28

Ser Thr Asn Lys Ala Val Val Ser Leu Ser
 1               5                  10

<210> SEQ ID NO 29
<211> LENGTH: 40
<212> TYPE: DNA
<213> ORGANISM: Artificial
<220> FEATURE:
<223> OTHER INFORMATION: epitope

<400> SEQUENCE: 29
ccggactagc tcagagaaac aacagctttg ttagtagaga                 40

<210> SEQ ID NO 30
<211> LENGTH: 41
<212> TYPE: DNA
<213> ORGANISM: Artificial
```

<220> FEATURE:
<223> OTHER INFORMATION: primer

<400> SEQUENCE: 30
gatccgatag tgacaatgat ctatcacttg aagatttctg a        41

<210> SEQ ID NO 31
<211> LENGTH: 37
<212> TYPE: DNA
<213> ORGANISM: Artificial
<220> FEATURE:
<223> OTHER INFORMATION: primer

<400> SEQUENCE: 31
tcagaaatct tcaagtgata gatcattgtc actatcg        37

<210> SEQ ID NO 32
<211> LENGTH: 32
<212> TYPE: PRT
<213> ORGANISM: Artificial
<220> FEATURE:
<223> OTHER INFORMATION: linker

<400> SEQUENCE: 32

Lys Leu Arg Ile Leu Gln Ser Thr Val Pro Ser Glu Arg Pro Gln Ala
1               5                   10                  15

Ser Gly Val Tyr Met Gly Asn Leu Thr Thr Arg Gly Pro Val Ala Thr
            20                  25                  30

<210> SEQ ID NO 33
<211> LENGTH: 667
<212> TYPE: PRT
<213> ORGANISM: Artificial
<220> FEATURE:
<223> OTHER INFORMATION: N-GFP fusion protein

<400> SEQUENCE: 33

Gly Ser His Met Ala Ser Met Thr Gly Gly Gln Gln Met Gly Arg Gly
1               5                   10                  15

Ser Met Ala Leu Ser Lys Val Lys Leu Asn Asp Thr Leu Asn Lys Asp
            20                  25                  30

Gln Leu Leu Ser Ser Ser Lys Tyr Thr Ile Gln Arg Ser Thr Gly Asp
        35                  40                  45

Ser Ile Asp Thr Pro Asn Tyr Asp Val Gln Lys His Ile Asn Lys Leu
    50                  55                  60

Cys Gly Met Leu Leu Ile Thr Glu Asp Ala Asn His Lys Phe Thr Gly
65                  70                  75                  80

Leu Ile Gly Met Leu Tyr Ala Met Ser Arg Leu Gly Arg Glu Asp Thr
                85                  90                  95

Ile Lys Ile Leu Arg Asp Ala Gly Tyr His Val Lys Ala Asn Gly Val
            100                 105                 110

Asp Val Thr Thr His Arg Gln Asp Ile Asn Gly Lys Glu Met Lys Phe
        115                 120                 125

Glu Val Leu Thr Leu Ser Ser Leu Thr Thr Glu Ile Gln Ile Asn Ile
    130                 135                 140

Glu Ile Glu Ser Arg Lys Ser Tyr Lys Met Leu Lys Glu Met Gly
145                 150                 155                 160

Glu Val Ala Pro Glu Tyr Arg His Asp Ser Pro Asp Cys Gly Met Ile
                165                 170                 175

Ile Leu Cys Ile Ala Ala Leu Val Ile Thr Lys Leu Ala Ala Gly Asp
            180                 185                 190

```
Arg Ser Gly Leu Thr Ala Val Ile Arg Arg Ala Asn Asn Val Leu Lys
        195                 200                 205

Asn Glu Met Lys Arg Tyr Lys Gly Leu Leu Pro Lys Asp Ile Ala Asn
    210                 215                 220

Ser Phe Tyr Glu Val Phe Glu Lys Tyr Pro His Phe Ile Asp Val Phe
225                 230                 235                 240

Val His Phe Gly Ile Ala Gln Ser Ser Thr Arg Gly Gly Ser Arg Val
                245                 250                 255

Glu Gly Ile Phe Ala Gly Leu Phe Met Asn Ala Tyr Gly Ala Gly Gln
            260                 265                 270

Val Met Leu Arg Trp Gly Val Leu Ala Lys Ser Val Lys Asn Ile Met
        275                 280                 285

Leu Gly His Ala Ser Val Gln Ala Glu Met Glu Gln Val Val Glu Val
        290                 295                 300

Tyr Glu Tyr Ala Gln Lys Leu Gly Gly Glu Ala Gly Phe Tyr His Ile
305                 310                 315                 320

Leu Asn Asn Pro Lys Ala Ser Leu Leu Ser Leu Thr Gln Phe Pro His
                325                 330                 335

Phe Ser Ser Val Val Leu Gly Asn Ala Ala Gly Leu Gly Ile Met Gly
            340                 345                 350

Glu Tyr Arg Gly Thr Pro Arg Asn Gln Asp Leu Tyr Asp Ala Ala Lys
        355                 360                 365

Ala Tyr Ala Glu Gln Leu Lys Glu Asn Gly Val Ile Asn Tyr Ser Val
    370                 375                 380

Leu Asp Leu Thr Ala Glu Glu Leu Glu Ala Ile Lys His Gln Leu Asn
385                 390                 395                 400

Pro Lys Asp Asn Asp Val Leu Glu Leu Lys Leu Arg Ile Leu Gln Ser
                405                 410                 415

Thr Val Pro Arg Ala Arg Asp Pro Pro Val Ala Thr Met Val Ser Lys
            420                 425                 430

Gly Glu Glu Leu Phe Thr Gly Val Val Pro Ile Leu Val Glu Leu Asp
        435                 440                 445

Gly Asp Val Asn Gly His Lys Phe Ser Val Ser Gly Glu Gly Glu Gly
    450                 455                 460

Asp Ala Thr Tyr Gly Lys Leu Thr Leu Lys Phe Ile Cys Thr Thr Gly
465                 470                 475                 480

Lys Leu Pro Val Pro Trp Pro Thr Leu Val Thr Thr Leu Thr Tyr Gly
                485                 490                 495

Val Gln Cys Phe Ser Arg Tyr Pro Asp His Met Lys Gln His Asp Phe
            500                 505                 510

Phe Lys Ser Ala Met Pro Glu Gly Tyr Val Gln Glu Arg Thr Ile Phe
        515                 520                 525

Phe Lys Asp Asp Gly Asn Tyr Lys Thr Arg Ala Glu Val Lys Phe Glu
    530                 535                 540

Gly Asp Thr Leu Val Asn Arg Ile Glu Leu Lys Gly Ile Asp Phe Lys
545                 550                 555                 560

Glu Asp Gly Asn Ile Leu Gly His Lys Leu Glu Tyr Asn Tyr Asn Ser
                565                 570                 575

His Asn Val Tyr Ile Met Ala Asp Lys Gln Lys Asn Gly Ile Lys Val
            580                 585                 590

Asn Phe Lys Ile Arg His Asn Ile Glu Asp Gly Ser Val Gln Leu Ala
        595                 600                 605

Asp His Tyr Gln Gln Asn Thr Pro Ile Gly Asp Gly Pro Val Leu Leu
```

```
                610                 615                 620
Pro Asp Asn His Tyr Leu Ser Thr Gln Ser Ala Leu Ser Lys Asp Pro
625                 630                 635                 640

Asn Glu Lys Arg Asp His Met Val Leu Leu Glu Phe Val Thr Ala Ala
                645                 650                 655

Gly Ile Thr Leu Gly Met Asp Glu Leu Tyr Lys
                660                 665

<210> SEQ ID NO 34
<211> LENGTH: 19
<212> TYPE: PRT
<213> ORGANISM: Artificial
<220> FEATURE:
<223> OTHER INFORMATION: linker

<400> SEQUENCE: 34

Lys Leu Arg Ile Leu Gln Ser Thr Val Pro Arg Ala Arg Asp Pro Pro
1               5                   10                  15

Val Ala Thr

<210> SEQ ID NO 35
<211> LENGTH: 680
<212> TYPE: PRT
<213> ORGANISM: Artificial
<220> FEATURE:
<223> OTHER INFORMATION: N-GFP fusion protein

<400> SEQUENCE: 35

Gly Ser His Met Ala Ser Met Thr Gly Gly Gln Gln Met Gly Arg Gly
1               5                   10                  15

Ser Met Ala Leu Ser Lys Val Lys Leu Asn Asp Thr Leu Asn Lys Asp
                20                  25                  30

Gln Leu Leu Ser Ser Ser Lys Tyr Thr Ile Gln Arg Ser Thr Gly Asp
            35                  40                  45

Ser Ile Asp Thr Pro Asn Tyr Asp Val Gln Lys His Ile Asn Lys Leu
50                  55                  60

Cys Gly Met Leu Leu Ile Thr Glu Asp Ala Asn His Lys Phe Thr Gly
65                  70                  75                  80

Leu Ile Gly Met Leu Tyr Ala Met Ser Arg Leu Gly Arg Glu Asp Thr
                85                  90                  95

Ile Lys Ile Leu Arg Asp Ala Gly Tyr His Val Lys Ala Asn Gly Val
            100                 105                 110

Asp Val Thr Thr His Arg Gln Asp Ile Asn Gly Lys Glu Met Lys Phe
        115                 120                 125

Glu Val Leu Thr Leu Ser Ser Leu Thr Thr Glu Ile Gln Ile Asn Ile
130                 135                 140

Glu Ile Glu Ser Arg Lys Ser Tyr Lys Lys Met Leu Lys Glu Met Gly
145                 150                 155                 160

Glu Val Ala Pro Glu Tyr Arg His Asp Ser Pro Asp Cys Gly Met Ile
                165                 170                 175

Ile Leu Cys Ile Ala Ala Leu Val Ile Thr Lys Leu Ala Ala Gly Asp
            180                 185                 190

Arg Ser Gly Leu Thr Ala Val Ile Arg Arg Ala Asn Asn Val Leu Lys
        195                 200                 205

Asn Glu Met Lys Arg Tyr Lys Gly Leu Leu Pro Lys Asp Ile Ala Asn
210                 215                 220

Ser Phe Tyr Glu Val Phe Glu Lys Tyr Pro His Phe Ile Asp Val Phe
225                 230                 235                 240
```

```
Val His Phe Gly Ile Ala Gln Ser Ser Thr Arg Gly Gly Ser Arg Val
                245                 250                 255

Glu Gly Ile Phe Ala Gly Leu Phe Met Asn Ala Tyr Gly Ala Gly Gln
                260                 265                 270

Val Met Leu Arg Trp Gly Val Leu Ala Lys Ser Val Lys Asn Ile Met
                275                 280                 285

Leu Gly His Ala Ser Val Gln Ala Glu Met Glu Gln Val Val Glu Val
                290                 295                 300

Tyr Glu Tyr Ala Gln Lys Leu Gly Gly Glu Ala Gly Phe Tyr His Ile
305                 310                 315                 320

Leu Asn Asn Pro Lys Ala Ser Leu Leu Ser Leu Thr Gln Phe Pro His
                325                 330                 335

Phe Ser Ser Val Val Leu Gly Asn Ala Ala Gly Leu Gly Ile Met Gly
                340                 345                 350

Glu Tyr Arg Gly Thr Pro Arg Asn Gln Asp Leu Tyr Asp Ala Ala Lys
                355                 360                 365

Ala Tyr Ala Glu Gln Leu Lys Glu Asn Gly Val Ile Asn Tyr Ser Val
                370                 375                 380

Leu Asp Leu Thr Ala Glu Leu Glu Ala Ile Lys His Gln Leu Asn
385                 390                 395                 400

Pro Lys Asp Asn Asp Val Leu Glu Leu Lys Leu Arg Ile Leu Gln Ser
                405                 410                 415

Thr Val Pro Ser Glu Arg Pro Gln Ala Ser Gly Val Tyr Met Gly Asn
                420                 425                 430

Leu Thr Thr Arg Gly Pro Val Ala Thr Met Val Ser Lys Gly Glu Glu
                435                 440                 445

Leu Phe Thr Gly Val Val Pro Ile Leu Val Glu Leu Asp Gly Asp Val
                450                 455                 460

Asn Gly His Lys Phe Ser Val Ser Gly Glu Gly Glu Gly Asp Ala Thr
465                 470                 475                 480

Tyr Gly Lys Leu Thr Leu Lys Phe Ile Cys Thr Thr Gly Lys Leu Pro
                485                 490                 495

Val Pro Trp Pro Thr Leu Val Thr Thr Leu Thr Tyr Gly Val Gln Cys
                500                 505                 510

Phe Ser Arg Tyr Pro Asp His Met Lys Gln His Asp Phe Phe Lys Ser
                515                 520                 525

Ala Met Pro Glu Gly Tyr Val Gln Glu Arg Thr Ile Phe Phe Lys Asp
                530                 535                 540

Asp Gly Asn Tyr Lys Thr Arg Ala Glu Val Lys Phe Glu Gly Asp Thr
545                 550                 555                 560

Leu Val Asn Arg Ile Glu Leu Lys Gly Ile Asp Phe Lys Glu Asp Gly
                565                 570                 575

Asn Ile Leu Gly His Lys Leu Glu Tyr Asn Tyr Asn Ser His Asn Val
                580                 585                 590

Tyr Ile Met Ala Asp Lys Gln Lys Asn Gly Ile Lys Val Asn Phe Lys
                595                 600                 605

Ile Arg His Asn Ile Glu Asp Gly Ser Val Gln Leu Ala Asp His Tyr
                610                 615                 620

Gln Gln Asn Thr Pro Ile Gly Asp Gly Pro Val Leu Leu Pro Asp Asn
625                 630                 635                 640

His Tyr Leu Ser Thr Gln Ser Ala Leu Ser Lys Asp Pro Asn Glu Lys
                645                 650                 655

Arg Asp His Met Val Leu Leu Glu Phe Val Thr Ala Ala Gly Ile Thr
```

-continued

```
            660                 665                 670
Leu Gly Met Asp Glu Leu Tyr Lys
            675                 680
```

The invention claimed is:

1. An isolated N protein-protein of interest fusion protein, wherein the N protein is a N protein of a virus of the Paramyxoviridae family and the protein of interest is fused in frame at the C-terminal end of the N protein,
wherein said virus of the Paramyxoviridae family is a virus of the Pneumovirinae subfamily, and wherein the protein of interest is a protein of vaccinal interest which is an antigen derived from a pathogenic microorganism.

2. An isolated N protein-protein of interest fusion protein, wherein the N protein is a N protein of a virus of the Paramyxoviridae family and the protein of interest is fused in frame at the C-terminal end of the N protein,
wherein said virus of the Paramyxoviridae family is a virus of the Pneumovirinae subfamily, and wherein the protein of interest is a construction comprising GFP fused in frame, at its C-terminal end, with a therapeutic or vaccinal protein.

3. A pharmaceutical composition comprising an isolated N protein-protein of interest fusion protein, wherein the N protein is a N protein of a virus of the Paramyxoviridae family and the protein of interest is fused in frame at the C-terminal end of the protein; or wherein the N protein is a N protein of a virus of the Paramyxoviridae family and the protein of interest is fused in frame at the C-terminal end of the protein and is obtainable by a method for preparing a N protein-protein of interest/P protein complex, the N and P proteins being proteins of a virus of the Paramyxoviridae family, said method comprising the steps of:

a) coexpressing a N protein of a virus of the Paramyxoviridae family, wherein the protein of interest is fused in frame at the C-terminal end of the N protein, with a P protein of the same virus of the Paramyxoviridae family;
b) collecting the so formed N protein-protein of interest/P protein complex, in a pharmaceutically acceptable carrier; and
c) separating the N protein-protein of interest fusion protein from the N protein-protein of interest/P complex,
wherein said virus of the Paramyxoviridae family is a virus of the Pneumovirinae subfamily and wherein the protein of interest is a protein of vaccinal interest which is an antigen derived from a pathogenic microorganism or a construction comprising GFP fused in frame, at its C-terminal end, with a therapeutic or vaccinal protein.

4. A method for producing the N protein-protein of interest fusion protein according to claim 1, said method comprising:
a) culturing a host cell containing an expression vector comprising a nucleic acid coding for the N protein-protein of interest fusion protein, wherein the N protein-protein of interest fusion protein is coexpressed with a P protein of the same virus of the Paramyxoviridae family;
b) collecting the so formed N protein-protein of interest/P protein complex; and
c) separating the N protein-protein of interest fusion protein from the N protein-protein of interest/P complex.

* * * * *